(12) United States Patent
Yousefi et al.

(10) Patent No.: US 10,206,612 B2
(45) Date of Patent: Feb. 19, 2019

(54) METHODS AND SYSTEMS FOR EXTRACTING VENOUS PULSATION AND RESPIRATORY INFORMATION FROM PHOTOPLETHYSMOGRAPHS

(71) Applicant: The Board of Regents, The University of Texas System, Austin, TX (US)

(72) Inventors: Rasoul Yousefi, Dallas, TX (US); Mehrdad Nourani, Plano, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 824 days.

(21) Appl. No.: 14/740,795

(22) Filed: Jun. 16, 2015

(65) Prior Publication Data

US 2015/0282746 A1 Oct. 8, 2015

Related U.S. Application Data

(63) Continuation-in-part of application No. 14/595,866, filed on Jan. 13, 2015, now Pat. No. 9,918,666.
(Continued)

(51) Int. Cl.
*A61B 5/1455* (2006.01)
*A61B 5/08* (2006.01)
(Continued)

(52) U.S. Cl.
CPC ...... *A61B 5/14551* (2013.01); *A61B 5/02416* (2013.01); *A61B 5/0816* (2013.01);
(Continued)

(58) Field of Classification Search
None
See application file for complete search history.

(56) References Cited

U.S. PATENT DOCUMENTS 6,246,897 B1 6/2001 Foo et al.
7,383,070 B2 6/2008 Diab et al.
(Continued)

FOREIGN PATENT DOCUMENTS

WO 20030063697 A1 8/2003

OTHER PUBLICATIONS

J. Lee, J.P. Florian, and K.H. Chon, "Respiratory Rate Extraction from Pulse Oximeter and Electrocardiographic Recordings," Physiol. Meas., vol. 32, No. 11, pp. 1763-1773, Nov. 2011.
(Continued)

*Primary Examiner* — Eric Winakur
*Assistant Examiner* — Marjan Fardanesh
(74) *Attorney, Agent, or Firm* — Schultz & Associates, P.C.

(57) ABSTRACT

A system and method for separating a venous component and an arterial component from a red signal and an infrared signal of a PPG sensor is provided. The method uses the second order statistics of venous and arterial signals to separate the venous and arterial signals. After reliable separation of the venous and the arterial component signals, the component signals can be used for different purposes. In a preferred embodiment, the respiratory signal, pattern, and rate are extracted from the separated venous component and a reliable "ratio of ratios" is extracted for $SpO_2$ using only the arterial component of the PPG signals. The disclosed embodiments enable real-time continuous monitoring of respiration pattern/rate and site-independent arterial oxygen saturation.

17 Claims, 12 Drawing Sheets

Related U.S. Application Data

(60) Provisional application No. 62/012,720, filed on Jun. 16, 2014, provisional application No. 61/926,773, filed on Jan. 13, 2014.

(51) Int. Cl.
    *A61B 5/00*     (2006.01)
    *A61B 5/024*    (2006.01)

(52) U.S. Cl.
    CPC ........ *A61B 5/7278* (2013.01); *A61B 5/02433* (2013.01); *A61B 5/7203* (2013.01); *A61B 5/7214* (2013.01); *A61B 5/7239* (2013.01); *A61B 5/7246* (2013.01)

(56) References Cited

U.S. PATENT DOCUMENTS

| | | | |
|---|---|---|---|
| 8,444,570 B2 | 5/2013 | McGonigle et al. | |
| 8,571,623 B2 | 10/2013 | Baker, Jr. et al. | |
| 2003/0088164 A1* | 5/2003 | Stetson | A61B 5/02416 600/323 |
| 2006/0241506 A1* | 10/2006 | Melker | A61B 5/08 600/529 |
| 2013/0079606 A1 | 3/2013 | McGonigle et al. | |
| 2013/0137936 A1 | 5/2013 | Baker, Jr. et al. | |
| 2013/0172767 A1 | 7/2013 | Dripps et al. | |

OTHER PUBLICATIONS

J. Lee and K.H. Chon, "Time-Varying Autoregressive Model Based Multiple Modes Particle Filtering Algorithm for Respiratory Rate Extraction from Pulse Oximeter," IEEE Trans. Biomed. Eng., vol. 58, No. 3, pp. 790-794, Mar. 2011.
P.A. Leonard, J.G. Douglas, N.R. Grubb, D. Clifton, P.S. Addison, and J.N. Watson, "A Fully Automated Algorithm for the Determination of Respiratory Rate from the Photoplethysmogram," J. Clin. Monit. Comput., vol. 20, No. 1, pp. 33-36, Feb. 2006.
Y.D. Lin, W.T. Liu, C.C. Tsai, and W.H. Chen, "Coherence Analysis Between Respiration and PPG Signal by Bivariate AR Model,"World Acad. Sci. Eng. Technol., vol. 3, No. 5, pp. 1168-1173, 2009.
K.V. Madhav, M.R. Ram, E.H. Krishna, K.N. Reddy, and K.A. Reddy, "Estimation of Respiration Rate from ECG, BP and PPG Signals Using Empirical Mode Decomposition," in Proc. 28th IEEE I2MTC, Hangzhou, China, pp. 1611-1664, May 10-12, 2011.
K.V. Madhav, M.R. Ram, E.H. Krishna, K.A. Reddy, and K.N. Reddy, "Estimation of Respiratory Rate from Principal Components of Photoplethysmographic Signals," in Proc. of 2010 IEEE EMBS conf. on Biomed. Eng. & Sciences, IECBES-2010, Kuala Lumpur, Malaysia, pp. 311-314, Nov./Dec. 2010.
K.V. Madhav, M.R. Ram, E.H. Krishna, and K.A. Reddy, "Monitoring Respiratory Activity Using PPG Signals by Order Reduced-Modified Covariance AR Technique," in Proc. 4th IEEE CBBE, Chengudu, China, pp. 1-4, Jun. 18-20, 2010.
K.V. Madhav, M.R. Ram, E.H. Krishna, N.R. Komalla, K.A. Reddy, "Robust Extraction of Respiratory Activity From PPG Signals Using Modified MSPCA," Instrumentation and Measurement, IEEE Transactions on , vol. 62, No. 5, pp. 1094-1106, May 2013.
A. Mahajan, E. Lee, A. Callom-Moldovan, "Intraoperative Use of Forehead Reflectance Oximetry in Pediatric Patients," Anesth Analg, 98(S7):A20, 2004 (abstract).
P.D. Mannheimer, M.P. O'Neil, E. Konecny, "The Influence of Larger Subcutaneous Blood Vessels on Pulse Oximetry," J Clin Monit Comp, vol. 18, No. 3, pp. 179-188, 2004.
Masimo Corp., "Signal extraction technology," (2012). [Online]. Available: http://www.masimo.com/pdf/whitepaper/LAB1035R.PDF.
MIT-BIH Arrhythmia Database. (2013). [Online]. Available: www.physionet.org/physiobank/database/mitdb.
G.B. Moody, R.G. Mark, A.L. Goldberger, "PhysioNet: a Web-Based Resource for the Study of Physiologic Signals," IEEE Engineering in Medicine and Biology Magazine, vol. 20, No. 3, pp. 70-75, May-Jun. 2001.
L. Nilsson, A. Johansson, and S. Kalman, "Monitoring of Respiratory Rate in Postoperative Care Using a New Photoplethysmographic Technique," J. Clin. Monit., vol. 16, No. 4, pp. 309-315, 2000.
L. Nilsson, A. Johansson, S. Kalman, "Respiration Can be Monitored by Photoplethysmography with High Sensitivity and Specificity Regardless of Anaesthesia and Ventilatory Mode," Acta Anaesthesiol Scand, vol. 49. pp. 1157-1162, 2005.
M.R. Ram, K.V. Madhav, E.H. Krishna, N.R. Komalla, K.A. Reddy, "A Novel Approach for Motion Artifact Reduction in PPG Signals Based on AS-LMS Adaptive Filter," IEEE Transactions on Instrumentation and Measurement, pp. 1-13, 2011.
K.A. Reddy, B. George, N. M. Mohan, V.J. Kumar, "A Novel Calibration-Free Method of Measurement of Oxygen Saturation in Arterial Blood," IEEE Transactions on Instrumentation and Measurement, vol. 58, No. 5, pp. 1699-1705, May 2009.
D.T. Redford, S.J. Barker, R.R. Lichtenthal, "Evaluation of 2 Forehead Reflectance Oximeters in Intraoperative Surgical Patients," Anesth, 101:A593, 2004 (abstract).
P.S. Addison, J.N. Watson, "Secondary Wavelet Feature Decoupling (SWFD) and its Use in Detecting Patient Respiration from the Photoplethysmogram," Engineering in Medicine and Biology Society, 2003. Proceedings of the 25th Annual International Conference of the IEEE, vol. 3, pp. 2602-2605, Sep. 17-21, 2003.
G.S. Agashe, J. Coakley, P.D. Mannheimer, "Forehead Pulse Oximetry: Headband Use Helps Alleviate False Low Readings Likely Related to Venous Pulsation Artifact," Journal of Anesthesiology, vol. 105, No. 6, pp. 1111-1116, Dec. 2006.
H.H. Asada, H. Jiang, and P. Gibbs, "Active Noise Cancellation using MEMS Accelerometers for Motion-Tolerant Wearable Bio-Sensors," in Proc. Conf. IEEE. Eng. Med. Biol. Soc., vol. 1, pp. 2157-2160, 2004.
H.H. Asada, P. Shaltis, A. Reisner, S. Rhee, R.C. Hutchinson, "Mobile Monitoring with Wearable Photoplethysmographic Biosensors," IEEE Engineering in Medicine and Biology Magazine, vol. 22, No. 3, pp. 28-40, May-Jun. 2003.
T. Aoyagi, M. Fuse, N. Kobayashi, K. Machida, K. Miyasaka, "Multiwavelength Pulse Oximetry: Theory for the Future," Anesth Analg., vol. 105, No. 6, 2007.
T. Aoyagi, K. Miyasaka, Pulse Oximetry: Its Invention, Contribution to Medicine, and Future Tasks, Anesth. Analg., vol. 94, pp. 51-53, 2002.
T. Aoyagi, "Pulse Oximetry: Its Invention, Theory, and Future," Journal of Anesthesia, vol. 17, No. 4, pp. 259-266, Jul. 2003.
A. Awad, M.A. Ghobashy, R.G. Stout, D.G. Silverman, K.H. Shelley, "How Does the Plethysmogram Derived from the Pulse Oximeter Relate to Arterial Blood Pressure in Coronary Artery Bypass Graft Patients?," Anesth Analg, vol. 93, pp. 1466-1471.
A.K. Barros, A. Cichocki, "Extraction of Specific Signals with Temporal Structure," Neural Computation, vol. 13, No. 9, pp. 1995-2003, 2001.
A.K. Barros, N. Ohnishi, "Heart Instantaneous Frequency (HIF): an Alternative Approach to Extract Heart Rate Variability," IEEE Trans. On Bio. Eng., vol. 48, No. 8, pp. 850-855, Aug. 2001.
A. Belouchrani, A. Abed-Meraim, J.F. Cardoso, E. Moulines, "A Blind Source Separation Technique Using Second-Order Statistics," IEEE Transactions on Signal Processing, vol. 45, No. 2, pp. 434-444, Feb. 1997.
V.F. Blanc, M. Haig, M. Troli, B. Sauve, "Computerized Photoplethysmography of the Finger," Can J Anaesth, vol. 40, pp. 271-278, 1993.
B. Bohnhorst, C.F. Poets, "Major Reduction in Alarm Frequency with a New Pulse Oximeter," Intensive Care Med, vol. 24, pp. 277-278, 1998.
P. Bonato, D. De Rossi, A. Dittmar, S. Jayaraman, I. Korhonen, A. Lymberis, E. Mc Adams, Y. Zhang, "IEEE EMBS Technical Committee on Wearable Biomedical Sensors and Systems: Position Paper," BSN, pp. 212-214, 2006.
R.D. Branson, P.D. Mannheimer, "Forehead Oximetry in Critically ill Patients: The Case for a New Monitoring Site," Respir Care Clin N Am, vol. 10, pp. 359-367, 2004.

(56) References Cited

OTHER PUBLICATIONS

R.T. Brouillette, J. Lavergne, A. Leimanis, G.M. Nixon, S. Ladan, C.D. McGregor, "Differences in Pulse Oximetry Technology can Affect Detection of Sleep-Disordered Breathing in Children," Anesth Analg vol. 94, pp. 47-53, 2002.
A. Casati, G. Squicciarini, M. Baciarello, M. Putzu, A. Salvadori, G. Fanelli, "Forehead Reflectance Oximetry: A Clinical Comparison with Conventional Digit Sensors during Laparotomic and Laparoscopic Abdominal Surgery," Journal of Clinical Monitoring and Computing, vol. 21, No. 5, pp. 271-276, 2007.
N.I. Cho, S.U. Lee, "Tracking Analysis of an Adaptive Lattice Notch Filter," IEEE Trans. on Circuits and Systems—II: Analog and Digital Signal Processing, vol. 42, No. 3, pp. 186-195, Mar. 1995.
H.M. Sami, B.S. Kleinman, V.A. Lonchyna, "Central Venous Pulsations Associated with a Falsely Low Oxygen Saturation Measured by Pulse Oximetry," Journal of Clinical Monitoring, vol. 7, No. 4. pp. 309-312, 1991.
P. Shaltis, H.H. Asada, "Monitoring of Venous Oxygen Saturation Using a Novel Vibratory Oximetry Sensor," Proceedings of the Second Joint 24th Annual Conference Engineering in Medicine and 24 Biology and the Annual Fall Meeting of the Biomedical Engineering Society, vol. 2, pp. 1722-1723, Oct. 2002.
K.H. Shelley, "Photoplethysmography: Beyond the Calculation of Arterial Oxygen Saturation and Heart Rate," Anesth Analg, vol. 105, No. 6, Dec. 2007.
K.H. Shelley, M. Dickstein, S.M. Shulman, "The Detection of Peripheral Venous Pulsation Using the Pulse Oximeter as a Plethysmograph," Journal of Clinical Monitoring, vol. 9, No. 4, pp. 283-287, 1993.
K.H. Shelley, D. Tamai, D. Jablonka, M. Gesquiere, R.G. Stout, D.G. Silverman, "The Effect of Venous Pulsation on the Forehead Pulse Oximeter Wave Form as a Possible Source of Error in SpO2 Calculation," Journal of Anesth Analg, vol. 100, pp. 743-747, 2005.
J.E Sinex, "Pulse Oximetry: Principles and Limitations," Amer. J. Emergency Med., vol. 17, No. 1, pp. 59-68, Jan. 1999.
H.A. Smithline, N. Rudnitzky, S. Macomber, F.S.J. Blank, "Pulse Oximetry Using a Disposable Finger Sensor Placed on the Forehead in Hypoxic Patients," The Journal of Emergency Medicine, vol. 39, No. 1, pp. 121-125, 2010.
Texas Instrument Inc., http://www.ti.com/tool/tmdxevm5515.
M. Wax, J. Sheinvald, "A Least-Squares Approach to Joint Diagonalization," IEEE Signal Processing Letters, vol. 4, No. 2, pp. 52-53, Feb. 1997.
J. G. Webster, Design of Pulse Oximeters, New York: Taylor & Francis, 1997, Chapter 4, Light Absorbance n Pulse Oxymetry, Oliver Wieben, pp. 40-41.
R.A. Whitman, M.E Garrison, T.J. Oestreich, M.S. Musumbi, "Evaluation of a New Reflectance Forehead Sensor in Detecting Oxygen Desaturation in Patients Undergoing Polysomnography," Anesthesiology, 99:A553, 2003 (abstract).
J.D. Wise, J.R. Caprio, T.W. Parks, "Maximum Likelihood Pitch Estimation," IEEE Trans. Acoust., Speech, Signal Processing, vol. 24, pp. 418-423, Oct. 1976.
L.B. Wood and H. Asada, "Low Variance Adaptive Filter for Cancelling Motion Artifact in Wearable Photoplethysmogram Sensor Signals," in Proc. Conf. IEEE Eng. Med. Biol. Soc., pp. 652-655, 2007.
M.M. Wood, L.E. Romine, Y.K. Lee, K.M. Richman, M.K. O'Boyle, D.A. Paz, P.K. Chu, D.H. Pretorius, "Spectral Doppler Signature Waveforms in Ultrasonography: a Review of Normal and Abnormal Waveforms," Ultrasound Q., vol. 26, No. 2, pp. 83-99, 2010.
J.Yong, A. Foo, S.J. Wilson, "A Computational System to Optimise Noise Rejection in Photoplethysmography Signals During Motion or Poor Perfusion States," Med Biol Eng Comput, vol. 44, pp. 140-145, Jan. 26, 2006.
J. Yong, A. Foo and S.J. Wilson, "Estimation of Breathing Interval from the Photoplethysmographic Signals in Children," Physiol. Meas., vol. 26, No. 6, pp. 1049-1058, Dec. 2005.
R. Yousefi, M. Nourani, S. Ostadabbas, I. Panahi, "A Motion-Tolerant Adaptive Algorithm for Wearable Photoplethysmographic Biosensors," Biomedical and Health Informatics, IEEE Journal of, vol. 18, issue 2, pp. 670-681, May 20, 2013.
R. Yousefi, M. Nourani, I. Panahi, "Adaptive Cancellation of Motion Artifact in Wearable Biosensors," Conf Proc IEEE Eng Med Biol Soc, pp. 2004-2008, Aug. 2012.
K.H. Chon, S. Dash, and K. Ju, "Estimation of Respiratory Rate from Photoplethysmogram Data Using Time-Frequency Spectral Estimation," IEEE Trans. Biomed. Eng., vol. 56, No. 8, pp. 2054-2063, Aug. 2009.
G. Cloete, P.R. Fourie, C. Scheffer, "Development and Testing of an Artificial Arterial and Venous Pulse Oximeter," 35th Annual International Conference of the IEEE Engineering in Medicine and Biology Society, pp. 4042-4045, Jul. 2013.
J.E. Cooke, J.E. Scharf, "Forehead Pulse Oximetry in the Trendelenburg Position," Anesthesiology,vol. 101, pp. A-583, 2004.
S. Dash, K.H. Shelley, D.G. Silverman, and K.H. Chon, "Estimation of Respiratory Rate from ECG, Photoplethysmogram, and Piezoelectric Pulse Transducer Signals: A Comparative Study of Time-Frequency Methods," IEEE Trans. Biomed. Eng., vol. 57, No. 5, pp. 1099-1107, May 2010.
J.C. Dorlas, J.A. Nijboer, "Photo-Electric Plethysmography as a Monitoring Device in Anaesthesia. Application and interpretation," Br J Anaesth, vol. 57, pp. 524-530, 1985.
C.G. Durbin, S.K. Rostow, "More Reliable Oximetry Reduces the Frequency of Arterial Blood Gas Analyses and Hastens Oxygen Weaning after Cardiac Surgery: a Prospective, Randomized Trial of the Clinical Impact of a New Technology," Crit Care Med, vol. 30, pp. 1735-1740, 2002.
A.S. Echiadis, V.P. Crabtree, J. Bence, L. Hadjinikolaou, C. Alexiou, T.J. Spyt, S. Hu, "Non-Invasive Measurement of Peripheral Venous Oxygen Saturation Using a New Venous Oximetry Method: Evaluation During Bypass in Heart Surgery," Physiological Measurement, vol. 28, No. 8, pp. 897-911, 2007.
S. Elliott, P. Darlington, "Adaptive Cancellation of Periodic, Synchronously Sampled Interference," IEEE Trans. on Acoustics, Speech and Signal Processing, vol. 33, No. 3, pp. 715-717, Jun. 1985.
[27] M. Fernandez, K. Burns, B. Calhoun, S. George, B. Martin, C. Weaver, "Evaluation of a New Pulse Oximeter Sensor," Am J Crit Care., vol. 16, No. 2, pp. 146-152, Mar. 2004.
Food and Drug Administration, "Pulse Oximeters-Premarket Notification Submissions [510(k)s] Guidance for Industry and Food and Drug Administration Staff," Mar. 2013.
J.M. Goldman, M.T. Petterson, R.J. Kopotic, S.J. Barker, "Masimo Signal Extraction Pulse Oximetry," J Clin Monit, vol. 16, pp. 475-483, 2000.
J.M. Graybeal, M.T. Petterson, "Adaptive Filtering and Alternative Calculations Revolutionizes Pulse Oximetry Sensitivity and Specificity During Motion and Low Perfusion," EMBC vol. 7, pp. 5363-5366, 2004.
H. Han, M.J. Kim, J. Kim, "Development of Real-Time Motion Artifact Reduction Algorithm for a Wearable Photoplethysmography," in Proc. Conf. IEEE Eng. Med. Biol. Soc., pp. 1538-1541, 2007.
J.A. Hirsch , B. Bishop, "Respiratory Sinus Arrhythmia in Humans: How Breathing Pattern Modulates Heart Rate," Am J Physiol., vol. 241, No. 4, pp. 620-629, 1981.
International Organization for Standardization, "Particular Requirements for Basic Safety and Essential Performance of Pulse Oximeter Equipment," 2011.
B. Jönsson, C. Lauren, T. Skau, L.G. Lindberg, "A New Probe for Ankle Systolic Pressure Measurement Using Photoplethysmography (ppg)," Ann Biomed Engl, vol. 33, pp. 232-239, 2005.
S.H. Kim, D.W. Ryoo, and C. Bae, "Adaptive Noise Cancellation Using Accelerometers for the PPG Signal from Forehead," in Proc. Conf. IEEE Eng. Med. Biol. Soc., pp. 2564-2567, 2007.
J. Lee and K.H. Chon, "An Autoregressive Model-Based Particle Filtering Algorithms for Extraction of Respiratory Rates as High as 90 Breaths Per Minute from Pulse Oximeter," IEEE Trans. Biomed. Eng., vol. 57, No. 9, pp. 2158-2167, Sep. 2010.

* cited by examiner

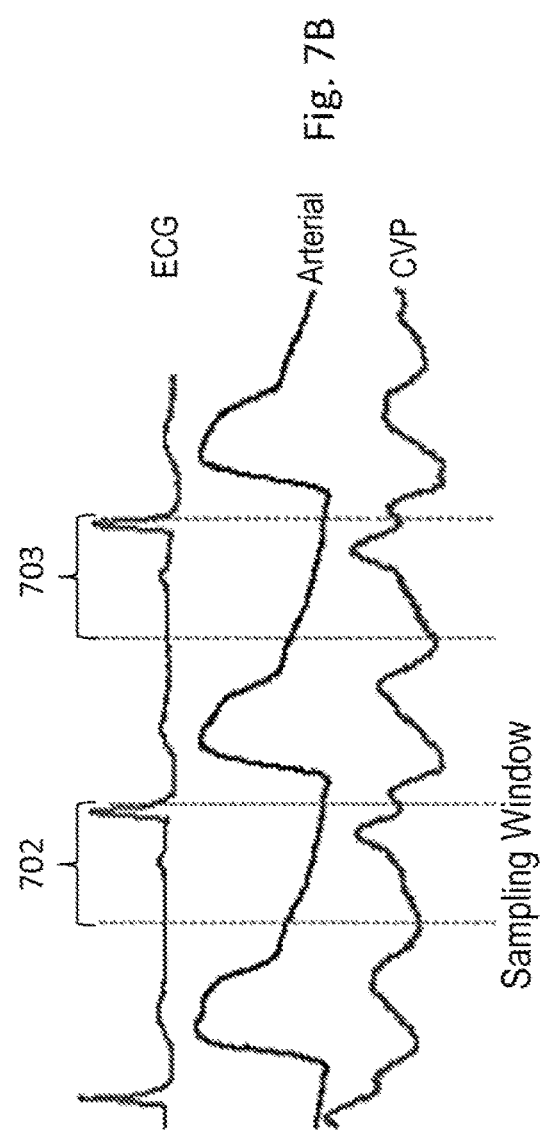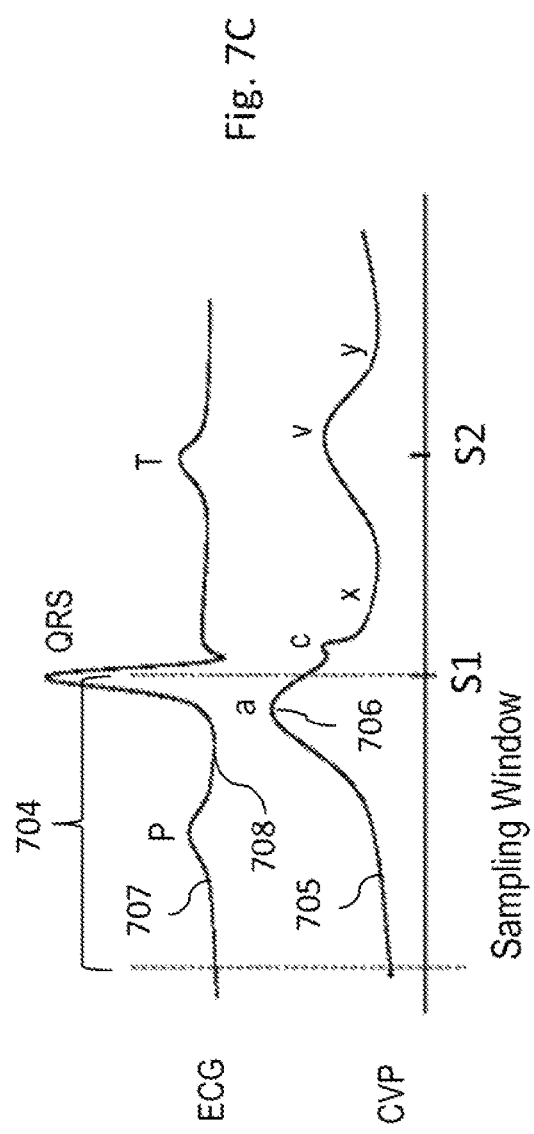

METHODS AND SYSTEMS FOR EXTRACTING VENOUS PULSATION AND RESPIRATORY INFORMATION FROM PHOTOPLETHYSMOGRAPHS

CROSS-REFERENCE TO RELATED APPLICATIONS

This application is a continuation in part of U.S. application Ser. No. 14/595,866 filed Jan. 13. 2015, which claims priority benefit from U.S. Provisional Application No. 61/926,773, filed Jan. 13, 2014. This application claims priority benefit from U.S. Provisional Application No. 62/012,720, filed Jun. 16, 2014. Each patent application identified above is incorporated herein by reference in its entirety to provide continuity of disclosure.

FIELD OF THE INVENTION

The present invention relates to monitoring a human's circulatory system. In particular, the present invention relates to arterial oxygen saturation monitoring and systems and methods for extracting information from photoplethysmographic sensors. The present invention further relates to healthcare, systems and methods for human health monitoring, and systems and methods for human circulation system monitoring.

BACKGROUND OF THE INVENTION

One of the main applications of photoplethysmographic (PPG) biosensors is measuring blood oxygen saturation. The commercial device based upon this technology is a pulse oximeter. Pulse oximetry may be used to quantify various blood flow characteristics including arterial oxygen saturation, the volume of blood pulsation carried to the tissues, and the heart rate. A pulse oximeter typically uses two light emitting diodes (LEDs) with wavelengths in red and infrared regions which emit light at a measurement site on a human body. A photodetector captures the transmitted or reflected light. The analog front-end hardware uses a time multiplexed approach with three phases: (i) an activated red LED phase, (ii) an activated infrared LED phase, and (iii) a dark phase. A transimpedance amplifier amplifies the current generated in the photodetector due to optical density during active phases and provides a voltage signal. The voltage signal is filtered, amplified, and sampled with an analog-to-digital converter for further processing.

At the measurement site (e.g. finger, ear, forehead, nasal), the tissue slightly expands during each heart beat as blood enters via arteries during systole. Then, the site contracts as blood leaves during diastole. As a result, the path length of the light will periodically change. Absorption is proportional to the optical path length according to the Lambert law of optical density and the blood volume change will be reflected in the output of the photodetector. Referring to FIG. 1, the light absorbance at sensor site 100 has three main signal components: a nonpulsatile component 101 originated from nonpulsatile blood, tissue pigmentation (e.g. skin, bone, muscle), which results in a direct current (DC) signal in the photodetector, a weaker signal 102 caused by blood return in veins, and a dominant alternating current (AC) 103 caused by blood volume change in arteries.

Light absorption is also a function of the hemoglobin concentration in blood and a "ratio of ratios" technique defines R as an intensity-independent parameter. When R is large, the blood saturation is low and vice versa. An empirical linear calibration curve relates the measured R to oxygen saturation where R is mathematically expressed as:

$$R = \frac{AC_R/DC_R}{AC_{IR}/DC_{IR}} \qquad \text{Eq. 1}$$

where, AC and DC are the ac and dc power of the PPG signals and indices R and IR refer to red and infrared, respectively. The existence of the venous component which has the information of blood return to the heart has been verified with different techniques, including imaging-based techniques, such as phase contrast magnetic resonance angiography.

PPG sensors also capture blood volume change in veins. The sensor's output AC current is a mixture of arterial and venous signals. Existence of the venous component causes the AC power of the PPG signals to change which leads to inaccuracy and false alarms in readings such as oxygen saturation level. In clinical settings, the venous signal has a significant effect on the shape of PPG signal and the $SpO_2$ readings. For example, a commercial forehead probe called The Nellcor™ manufactured by Covidien LP of Mansfield, Mass. needs to be placed above the eyebrow using a self-adhesive bandage. However, this forehead sensor is limited to low saturation readings. In hospital settings using finger, forehead, and ear sensors, a complex waveform can be created by the prominent venous component. However, the power of the venous component signal differs in various sensor sites, leading to inaccurate readings. This inaccuracy is confirmed by applying a pressure dressing to the measurement site, which weakens the effect of the venous signal on the PPG signal.

As seen, venous pulsation remains one of the sources of inaccuracy in various applications of PPG sensors such as arterial oxygen saturation. Researchers have collected clinical data on effect of venous signal/pulsation on PPG signal or pulse oximetry readings. Generally, researchers have observed occurrences of venous signal pulsation on PPG signals and attempted to understand how such pulsation affects the oxygen saturation readings. The main experimental solution suggested has been control of pressure on the sensor during signal acquisition.

The prior art has attempted to address these problems associated with venous signal pulsation with limited success. For example, the system for pulse oximetry from Covidien defines and adjusts the sensitivity level of a PPG sensor. The sensitivity level is adjusted based on the location of the measurement displayed to the user. The system also compares the current R value to historical R values. The historical value may include measurements from the same patient or an average value from other patients. However, in the Covidian system, once a prominent venous is detected, the reading is stopped or ignored. This is a problem because, in many applications, such as under anesthesia during surgery, the intermittent and temporary changes of the oxygen saturation need to be constantly monitored which cannot occur if the readings are stopped.

Other methods of the prior art include extracting information from venous pulsation of the PPG signal by adding a mechanical vibrator to the sensing part. The mechanical vibrator works as an actuator that creates an external artificial perturbation close to the PPG sensor. A pressure transducer is attached at a first site and applies a drive signal at a predetermined frequency. The drive signal causes a series of pulsations of a predetermined magnitude in the veins. Then, variations in blood volume in veins are captured by an optical sensor and used to estimate venous oxygen saturation. However, in order for the system to function, an artificial pulsation is needed from a mechanical source. Since this pulsation is artificial, it does not provide any insight into the actual blood return and natural venous functionality.

Based on the negative role of venous pulsation on signal accuracy, there is a need in the art for a system and method for extracting venous pulsation from PPG sensors. There is a need in the art for a system and method that addresses the inaccuracy in measurement of parameters, such as $SpO_2$, by extracting a high-quality venous signal. There is a further need in the art for a system and method that uses the extracted venous signal on PPG, by extracting other medically relevant information, such as respiration rate.

SUMMARY

A system and method for separating a venous component and an arterial component from a red signal and an infrared signal of a PPG sensor is provided. The method uses the second order statistics of venous and arterial signals to separate the venous and arterial signals. After reliable separation of the venous and the arterial component signals, the component signals can be used for different purposes. In a preferred embodiment, the respiratory signal and rate are extracted from the separated venous component and a reliable "ratio of ratios" is extracted for $SpO_2$ using only the arterial component of the PPG signals. The disclosed embodiments enable real-time continuous monitoring of respiration pattern/rate and site-independent arterial oxygen saturation.

BRIEF DESCRIPTION OF THE DRAWINGS

In the detailed description of the preferred embodiments described below, reference is made to the accompanying drawings.

FIG. 7B is a graph of a venous signal sampling window.

FIG. 7C is a graph of a venous signal sampling window.

DETAILED DESCRIPTION

It will be appreciated by those skilled in the art that aspects of the present disclosure may be illustrated and described in any of a number of patentable classes or contexts including any new and useful process or machine or any new and useful improvement. Aspects of the present disclosure may be implemented entirely in hardware, entirely in software (including firmware, resident software, micro-code, etc.) or combining software and hardware implementation that may all generally be referred to herein as a "circuit," "module," "component," or "system." Further, aspects of the present disclosure may take the form of a computer program product embodied in one or more computer readable media having computer readable program code embodied thereon.

Figure 1:
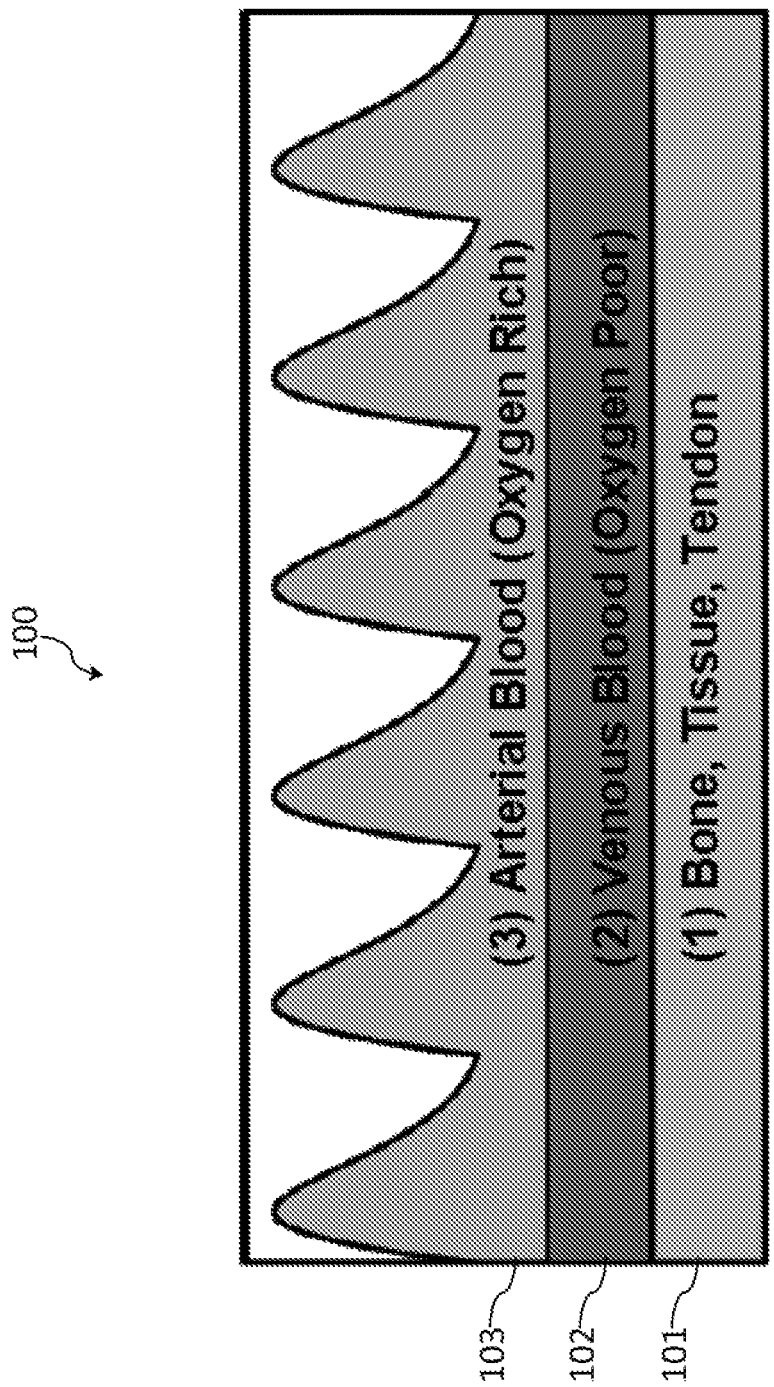
FIG. 1 is a diagram of different components of a captured PPG signal.
Figure 2A:
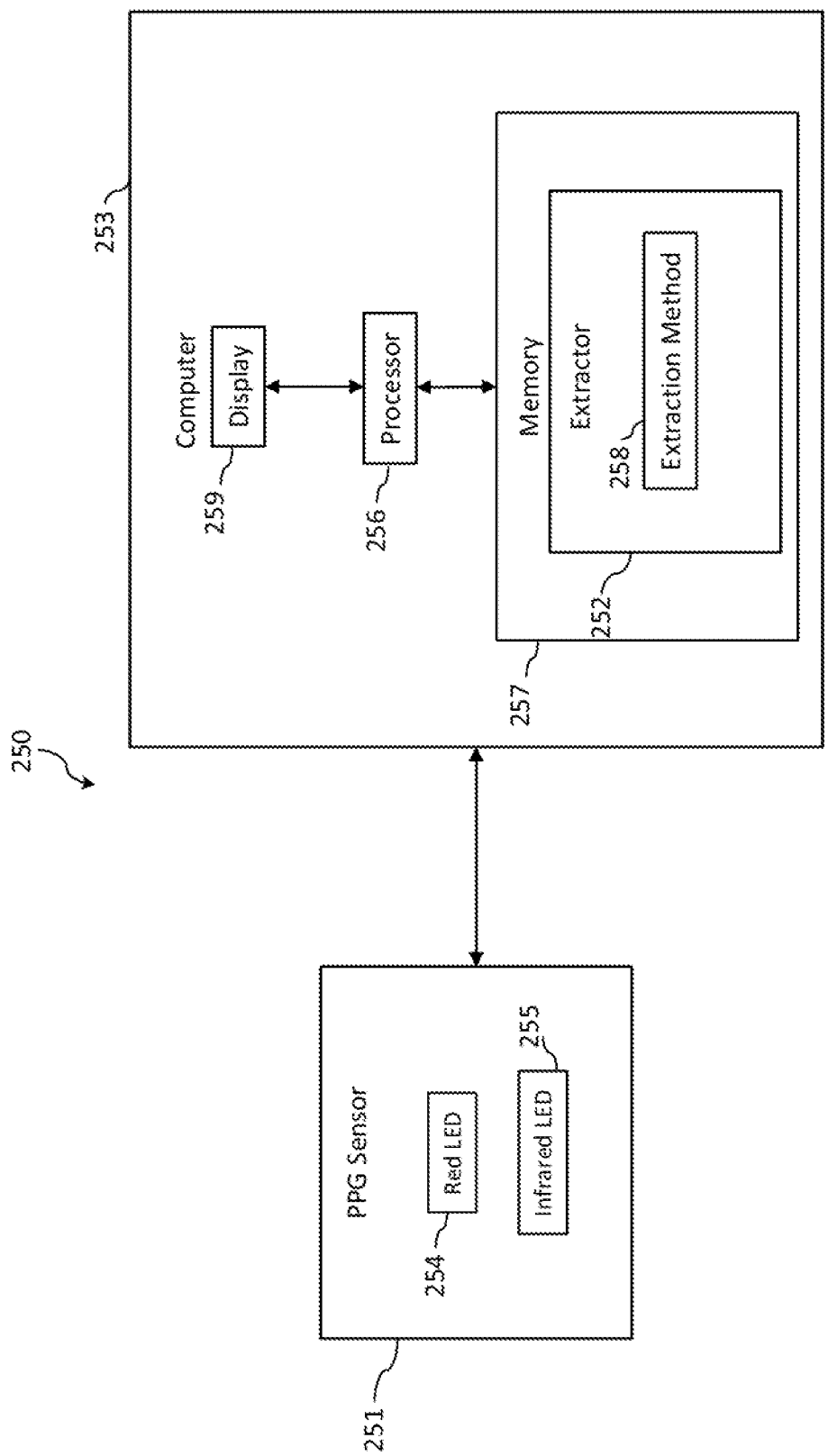
FIG. 2A is a schematic of an extraction system of a preferred embodiment.

Referring to FIG. 2A, system 250 includes PPG sensor 251 connected to computing device 253. PPG sensor 251 includes red LED 254 and infrared LED 255. Computing device 253 includes processor 256, memory 257 connected to processor 256, and display 259 connected to processor 256. Extractor 252 is saved in memory 257 and is executed by processor 256. Extractor 252 includes extraction method 258, as will be further described below. In a preferred embodiment, extractor 252 receives a red signal from red LED 254 and an infrared signal from infrared LED 255. Extractor 252 processes the red signal and the infrared signal according to extraction method 258, as will be further described below.

In one embodiment, computing device 253 is a personal computer. In another embodiment, computing device 253 is a tablet computer. In another embodiment, computing device 253 is a smartphone. Any computing device known in the art may be employed.

In one embodiment, computing device 253 is a wearable device, including a wrist-worn device or an electronic patch. In this embodiment, processor 256 and memory 257 are embedded. Any wearable computing device known in the art may be employed.

In a preferred embodiment, display 259 is an organic light-emitting diode ("OLED") digital display. Any suitable display type known in the art may be employed.

In a preferred embodiment, extractor 252 is a set of software modules including a set of filters and multipliers, executable by any processor. Any type of implementation known in the art, including software implementations, hardware implementations, and any combinations thereof may be employed.

The operation of PPG biosensors is described by the Beer-Lambert law wherein transmitted light, I, resulting from an incident source light, $I_0$, traveling through a substance with concentration c and path length l at the site of measurement, is modeled as:

$$I = I e^{-\varepsilon(\lambda)cl} \qquad \text{Eq. 2}$$

where $\varepsilon$ is called the extinction coefficient of the absorbance substance at the site of measurement and is a function of the wavelength $\lambda$. The optical density, $A=\varepsilon(\lambda)cl$, is the negative natural log of the transmitted light $I_0$ to incident light defined for both scatterer and non-scatterer. The Schuster's theory of optical scattering has been applied to pulse oximetry which provides more insight to the improvement of the pulse oximeters compared to the Beer-Lambert law which gives an approximate estimation about scatterer. The optical density changes ($\Delta A$) resulting from arterial blood thickness change, $\Delta D_a$, is:

$$\Delta A_a = \sqrt{E_a(E_a+F)} Hb_a \Delta D_a \qquad \text{Eq. 3}$$

where $E_a = S_a E_o + (1-S_a)E_r$, F is the scattering coefficient, $E_o$ is the extinction coefficient of oxyhemoglobin, $E_r$ is the extinction coefficient of deoxyhemoglobin and $S_a$ is the oxygen saturation rate. When measured in at least two-wavelengths, this optical density change is used to derive parameters such as $SpO_2$. However, the venous pulsation will be present in the measured optical density and affect the quality and reliability of the measurement. When more than one substance (e.g. vein with variable blood volume) absorbs light in a medium, the total optical density is modeled as:

$$\Delta A = \sqrt{E_a(E_a+F)} H b_a \Delta D_a + \sqrt{E_v(E_v+F)} H b_v \Delta D_v \quad \text{Eq. 4}$$

where indices a and v denote artery and vein, respectively. Tissue pigmentation including skin, bone and muscle results in wavelength-independent fixed absorption which can be removed or has no effect on the parameter extraction. To formulate the problem, assume that a two wavelength PPG sensor producing two mixed signals $x_r(n)$ and $x_{ir}(n)$ corresponding to red and infrared LEDs, respectively, and optical density changes of $\Delta A_r(n)$ and $\Delta A_{ir}(n)$, respectively. $x_r(n)$ and $x_{ir}(n)$ are linear combinations of arterial and venous component signals where the extinction coefficient is different at each wavelength. The observation signal corresponding to LEDs is written as:

$$x(n) = A\ s(n) \quad \text{Eq. 5}$$

where $x(n)=[x_r(n) x_{ir}(n)]^T$ is the PPG sensor's output corresponding to different wavelengths, $s(n)=[s_a(n) s_v(n)]^T$ is a vector including the of arterial signal and venous noise source and A is the 2×2 mixing matrix.

Every major vessel in the human body has a flow pattern characteristic that is visible in a time domain signal. These patterns that are representable in modalities such as spectral waveforms obtained with Doppler ultrasonography have been used as diagnosis tools in current practices. As a result, there is a time coherence and structure in source signals $s(n)$ coming from the vein and the artery of the measurement site. This time coherence and structure will be reflected in the second order statistics (e.g. autocorrelation) of the source signals and thus is considered as second order stationary signal in the time interval of measurement.

Given the linear IVA mixing model of Eq. 5, an unsupervised data analysis technique is applied, namely, Blind Source Separation (BSS), to process the two-channel recording of PPG signals. The BSS technique uses observed signals x and the IVA mixing model in Eq. 5 to extract underlying sources of the mixed signals. The solution to the BSS problem is found by approximating the generalized eigenvectors of a set of target matrices representing signal statistics. Therefore, the blind source separation of arterial and venous source signals is accomplished by solving a joint diagonalization problem. Given a set of k target matrices of size N×N (i.e., $C_1, C_2, \ldots, C_k$), the joint diagonalization problem finds a nonsingular matrix V such that the transformed matrices $VC_kV^T$ becomes as diagonal as possible for all k values. By suitably defining the target matrices of the observation x, the time coherence and time structure of arterial and venous source signals are used to separate the observed mixture.

Second order statistics of the source signals which capture the time structure and coherence of vein and arterial source signals are used to define the target matrices. Covariance matrices $C_\tau(x)$ of the delayed mixed signals are employed for joint diagonalization in BSS. Thus, $C_\tau(x)$ is defined as:

$$C_\tau(x) = {}^d E\{x(t)x(t+\tau)^T\} \quad \text{Eq. 6}$$

and is used as a target matrix where E is the expectation over time t and $\tau$ is a shift in time domain. Using the IAV mixing model in Eq. 5, it is shown that the covariance of mixed observation signals, x, is related to covariance of source signals s by:

$$C_\tau(x) = A C_\tau(s) A^T \quad \text{Eq. 7}$$

where off diagonal cross correlation elements of $C\tau(s)$ are zero due to lack of correlation among source signals and $C\tau(s)$ is assumed to be a diagonal matrix. Hence, mixing matrix A in the BSS problem is found by diagonalizing the covariance matrices $C\tau(x)$. Assuming A is invertible, this is expressed as:

$$C_\tau(s) = V C_\tau(x) V^T \quad \text{Eq. 8}$$

where V diagonalizes all target matrices $C\tau(x)$ simultaneously. This means that the problem of venous noise effect in the PPG signal is converted to a BSS problem. The BSS problem is effectively solved by approximate joint diagonalization (AJD) of time-lagged covariance matrices of mixed PPG observation signal in two red and infrared wavelengths. In order to solve AJD problem, a two stage algorithm called Second Order Blind Identification (SOBI) is used, as described below.

Figure 2B:
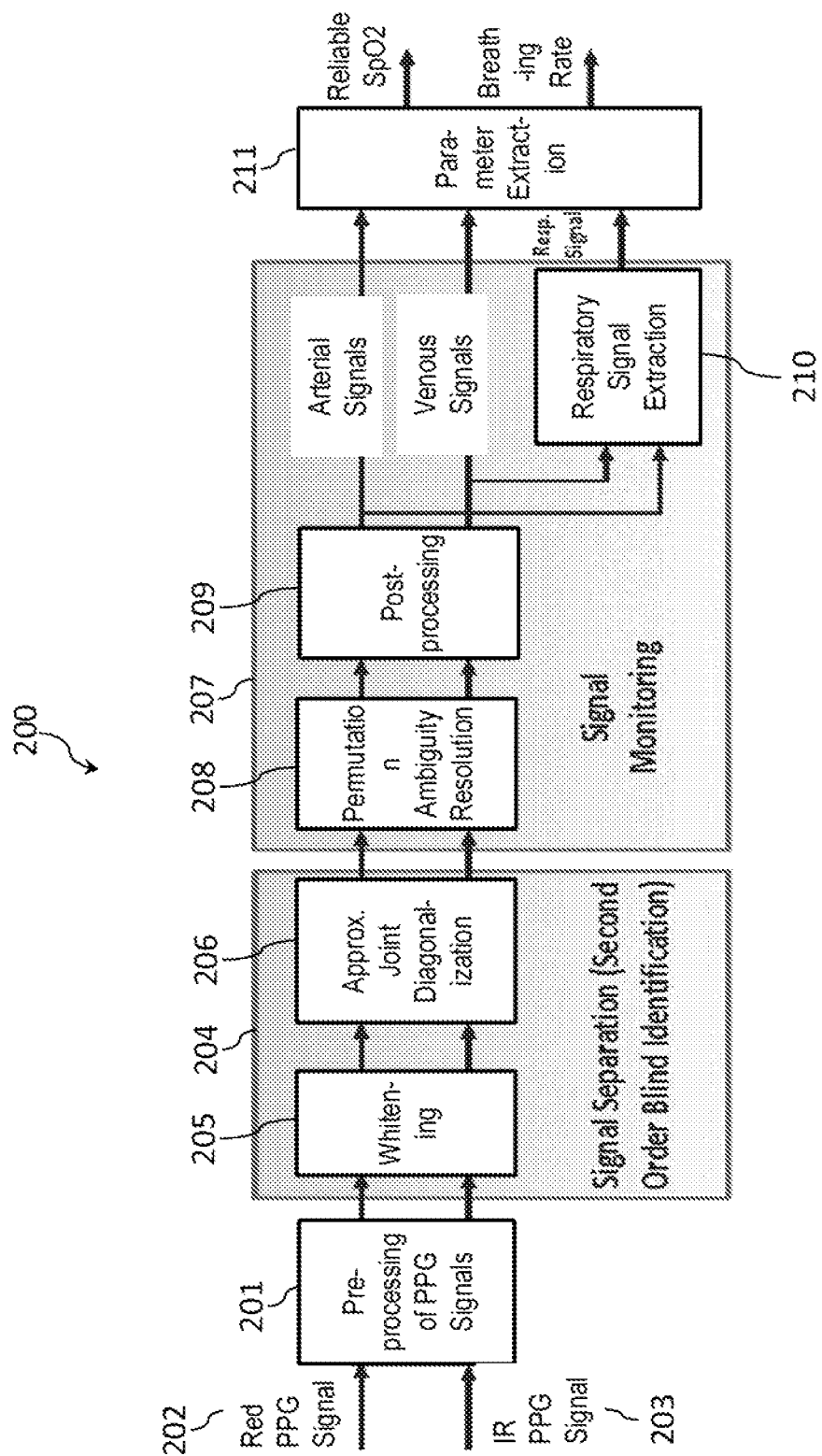
FIG. 2B is a flowchart of a method of a preferred embodiment.

Referring to FIG. 2B, method 200 for extracting venous and pulsation and respiratory information is described. In step 201, a low pass filter is applied on a red channel and an infrared channel to remove unwanted frequency content of red PPG signal 202 and infrared PPG signal 203 in a preprocessing step. In one embodiment, red PPG signal 202 and infrared PPG signal 203 may be corrupted by motion. In step 204, the SOBI technique separates the arterial and venous signal components. The SOBI technique in step 204 uses the diagonalization of several covariance matrices.

In step 205, a whitening step is performed. The sensor signals $x_r(n)$ and $x_{ir}(n)$ are generally mutually correlated and the covariance matrix is a full but not diagonal matrix. "Prewhitening" is accomplished by singular value decomposition of the covariance matrix at time lag $\tau=0$. Prewhitening is applied on mixed signal vector x(n) to prepare input signals for robust separation. The sensor signals x(n) is processed by the following transformation:

$$y(n) = W x(n) \quad \text{Eq. 9}$$

and the covariance matrix of zero mean vector y becomes:

$$E\{y(n)y(n)^T\} = W C_0(x) W^H = W A A^H W^H = I_2 \quad \text{Eq. 10}$$

where $I_2$ is a unity 2×2 matrix as a result of this transformation. Consequently, for the whitening matrix W, a unitary matrix L exists such that WA=L and hence:

$$A = W^{-1} L \quad \text{Eq. 11}$$

where $W^{-1}$ is the inverse of W.

Exploiting the time structure of source signals, the unitary factor L is obtained from covariance matrices at non-zero time lags, in other words:

$$C_\tau(y) = W C_\tau(x) W^H \quad \text{Eq. 12}$$

where $C_\tau(y)$ is the covariance matrix of y, whitened red and infrared observation signals. Using Equations (7) and (11), we have $C_\tau(y) = L C_\tau(s) L^H$. This means that L can be obtained as a unitary diagonalizing matrix $C_\tau(y)$ for non-zero lag $\tau$.

SOBI technique uses this fact with a set of lagged covariance matrices $C = [C_{\tau 1}(y), \ldots, C_{\tau k}(y)]$ where $C_{\tau 2}(y)$ $i = 1, \ldots k$ is a covariance matrix of y at lag $\tau_i$. This technique defines a cost function:

$$Q(C,V) = \Sigma_{i=1}^k \text{Off}(V^H C_{\tau i} V) \quad \text{Eq. 13}$$

for joint diagonalization of the lagged covariance matrices. $\text{Off}(V^H C_{\tau i} V)$ is the summation of square of absolute value of off diagonal elements in $C_{\tau i}$. Minimization of cost function Q leads to approximate joint diagonalization of covariance matrices where it uses information of a set of covariance matrices and it is not required that all $C_{\tau i}$'s be exactly simultaneously diagonalized. There are different numerically efficient techniques for computation of AJD.

In step 206, a Jacobi technique is generalized for minimization of Q and finding the unitary matrix L. The generalized Jacobi approach computes L using the product of given rotations. Step 205 provides matrix W and step 206 finds the unitary matrix L for computation of mixing matrix A in Eq. 11. Arterial and venous components are separated by the SOBI technique in step 204. However, a permutation indeterminacy resolution is needed to label the arterial and venous components because it is not known which of the outputs is related to the artery and which one to the vein.

In step 207, the arterial and venous signal components are monitored. In step 208, a permutation ambiguity technique is added to the separated arterial and venous components to label the arterial and venous components.

The BSS process factors the mixed observed signal x into a mixing matrix A and a vector s. A scalar factor is exchanged between $s_a(n)$ and $s_v(n)$ in s and the corresponding columns of A. This is called "scaling ambiguity" which means that the amplitude of the source signals is not uniquely defined. In other words, the mixing matrix is rewritten as:

$$x = As = \sum_{j=1}^{N} A_j s = \sum_{j=1}^{N} (\alpha_j A_j)(1/\alpha_j s)$$ Eq. 14 where $A_j$ is the $j^{th}$ column of matrix A. Moreover, this means that the sign of the sources cannot be derived. Similarly, there is also a permutation ambiguity meaning that the order of the sources is not unique. This is because equation:

$$x = AP^{-1} Ps$$ Eq. 15 is indistinguishable from Eq. 5, where here P is a permutation matrix.

This results in separation of the arterial and venous signals with the linear system of the form:

$$\begin{cases} s_1(n) = h_{11} x_r(n) + h_{12} x_{ir}(n) \\ s_2(n) = h_{21} x_r(n) + h_{22} x_{ir}(n) \end{cases}$$ Eq. 16 where h is a demixing matrix derived from AJD of second order statistics. Due to permutation ambiguity, it is not known which source ($s_1$ or $s_2$) is the arterial source.

In order to automatically find arterial and venous components after separation, time domain characteristics of arterial and venous components are used. Venous and arterial signals have different time domain behaviors, and so the statistical properties of these two signals are different. Kurtosis of $s_1$ and $s_2$ are shown labeled as $K_{s1}$ and $K_{s2}$. The arterial signal is more correlated to a sinusoidal signal. So, the absolute value of difference of each source and 1.5 (kurtosis of sinusoidal) is computed, i.e. $\delta_{source} = |K_{source} - 1.5|$. Therefore, the 2×2 permutation matrix P is defined to be a unity matrix when $\delta s_1 < \delta s_2$, and $$P = \begin{pmatrix} 0 & 1 \\ 1 & 0 \end{pmatrix}$$ Eq. 17 otherwise. In other embodiments, similar time domain features such as skewness or power analysis of signal in frequency domain may be used for labeling the arterial and venous signals.

Returning to FIG. 2B, in step 210 a respiratory signal is extracted using separated venous and arterial signals, which will be described further. In step 211, after extracting the respiratory signal, a correlation-based respiration rate extractor is used to extract the respiration (e.g., breathing) rate.

Figure 3:
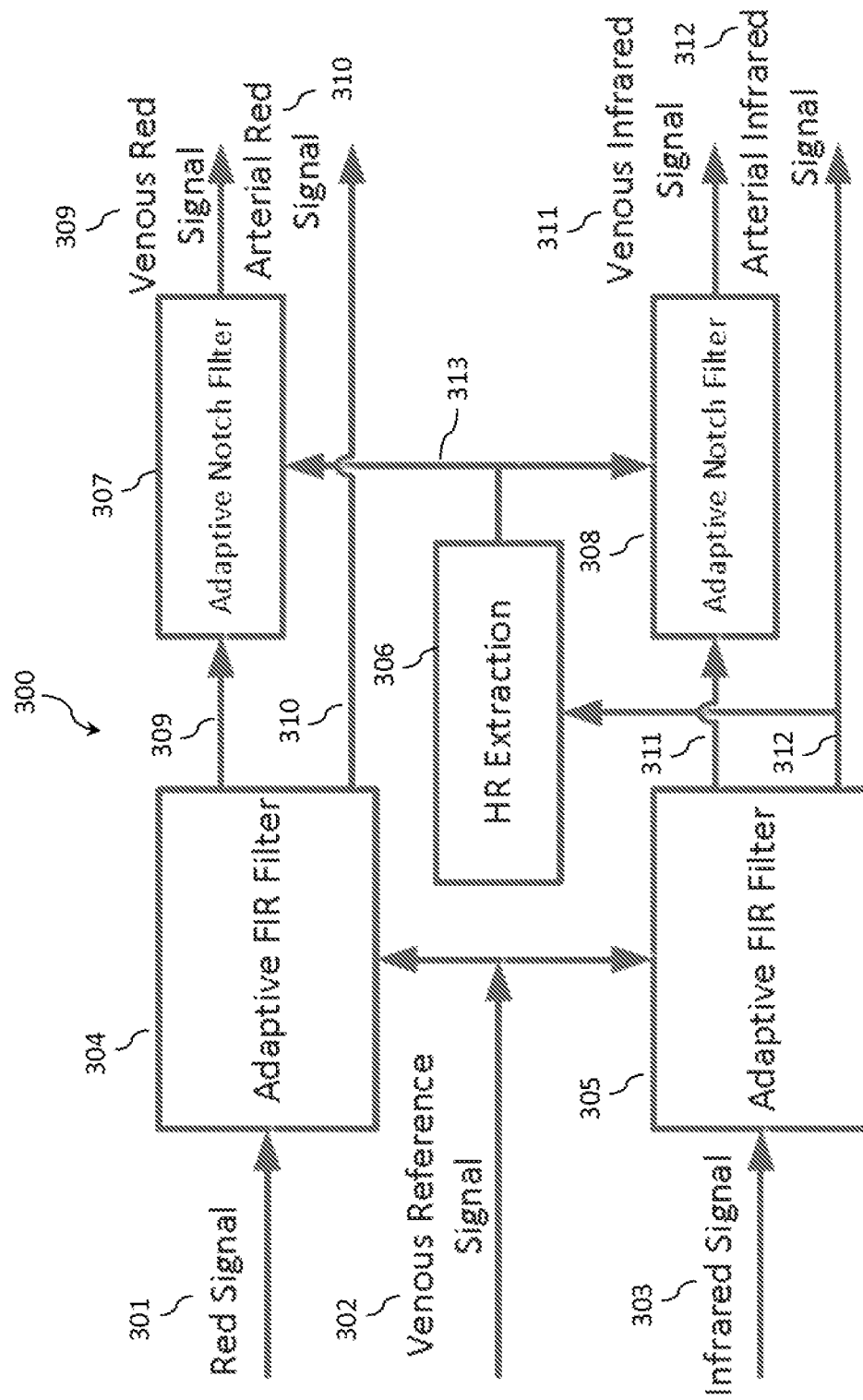
FIG. 3 is a schematic of a postprocessing method of a preferred embodiment.

Referring to FIG. 3, post processing step 209 is performed using set of filters 300. Venous reference component 302 is now used as a reference noise source in adaptive filters 304 and 305 to separate arterial and venous portions of the signal from input red and infrared signals 301 and 303, respectively. Adaptive filter 304 receives red signal 301 and venous reference component 302 and outputs venous red signal 309 and arterial red signal 310. Adaptive filter 305 receives infrared signal 303 and venous reference component 302 and outputs venous infrared signal 311 and arterial infrared signal 312.

Figure 4:
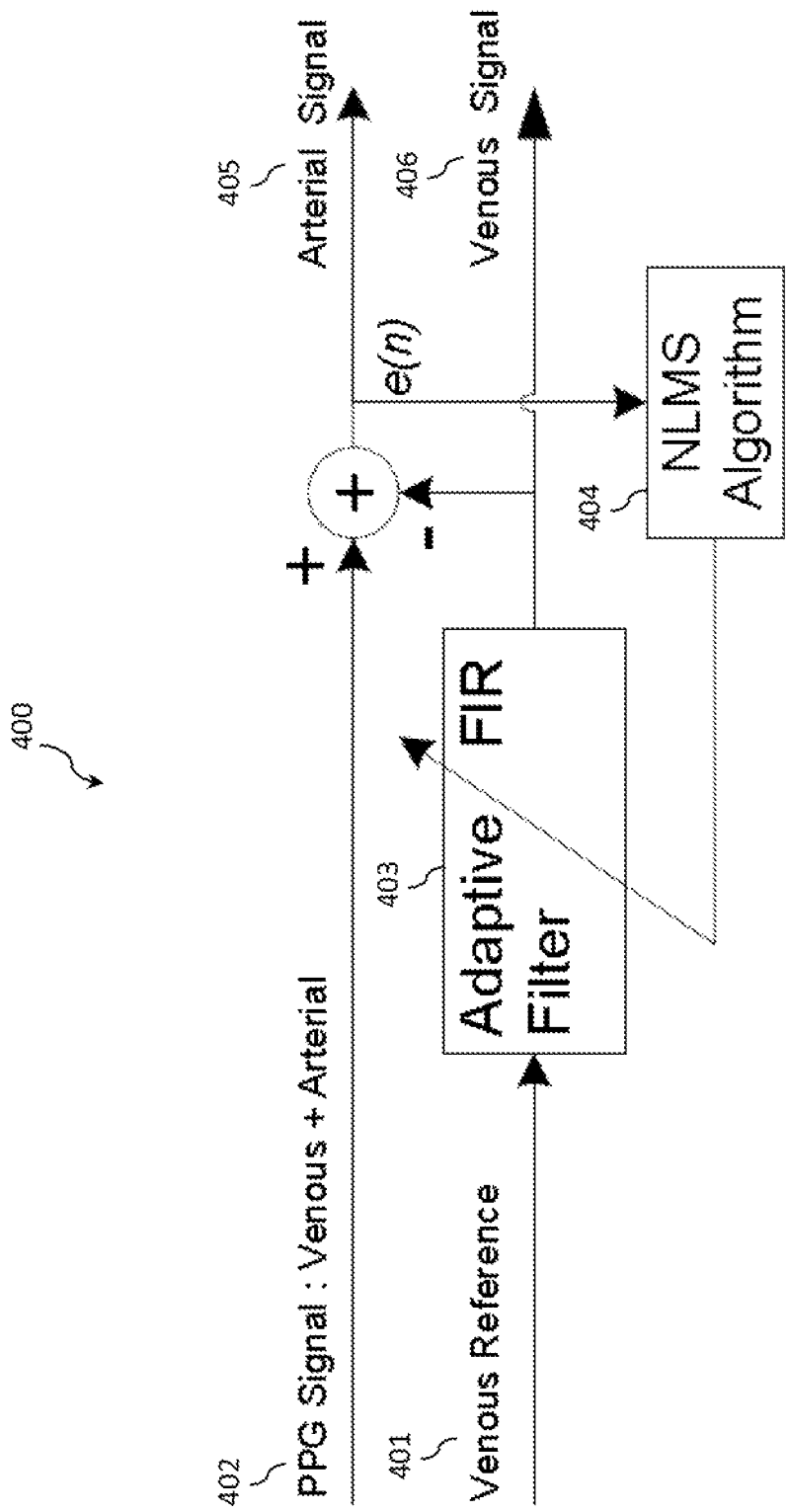
FIG. 4 is a schematic of an adaptive filter used in the postprocessing method.

Referring to FIG. 4, each of adaptive filters 304 and 305 are further described. Each filter 403 receives venous reference source 401 and PPG mixed signal 402 and provides two output signals, venous signal 406 and arterial signal 405. Algorithm 404 controls filter 403 to separate venous signal 406 and arterial signal 405.

Returning to FIG. 3, arterial red and infrared signals 310 and 312 will be used for monitoring $SpO_2$. Each of venous signals 309 and 311 is filtered with notch filter 307 and 308, respectively, to suppress the signal power in fundamental frequency 313 of the PPG signal.

Each of notch filters 307 and 308 of a preferred embodiment is an adaptive comb filter, timing the location of zeros and poles with fundamental frequency (e.g., Heart Rate) 313 of the signal. Fundamental frequency 313 is extracted at 306 using an autocorrelation based technique and arterial infrared signal 312. Fundamental frequency 313 is used in transfer function:

$$H(z) = \frac{(1 + \alpha z^{-1} + z^{-2})}{(1 + \rho \alpha z^{-1} + \rho^2 z^{-2})}$$ Eq. 18 which has two zeros at $e^{\pm jk\omega}_0$ on the unit circle and two poles on with the same angle and radii of $\rho$ in the range of about 0.95 to 0.995.

Figure 5B:
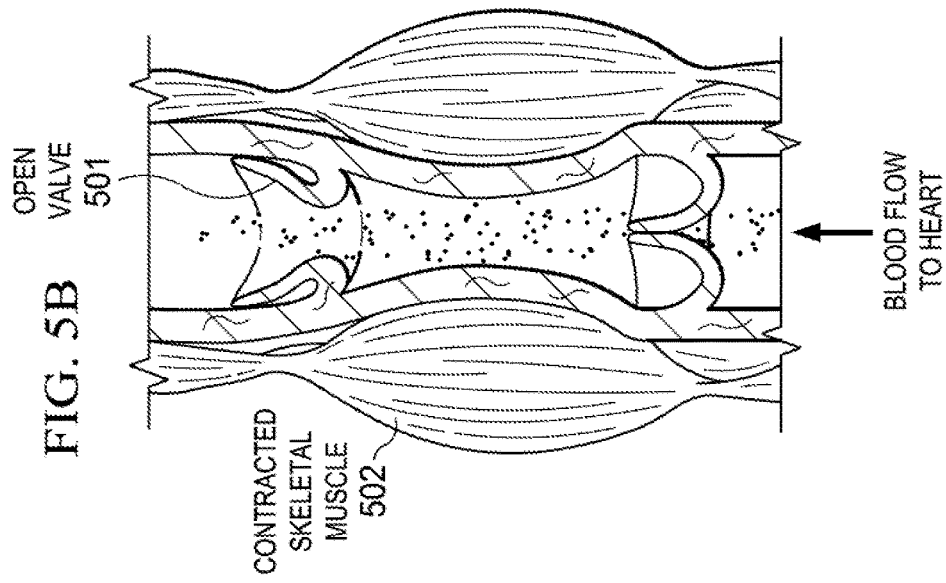
FIG. 5B is a diagram of a venous return during a muscle pump.
Figure 5A:
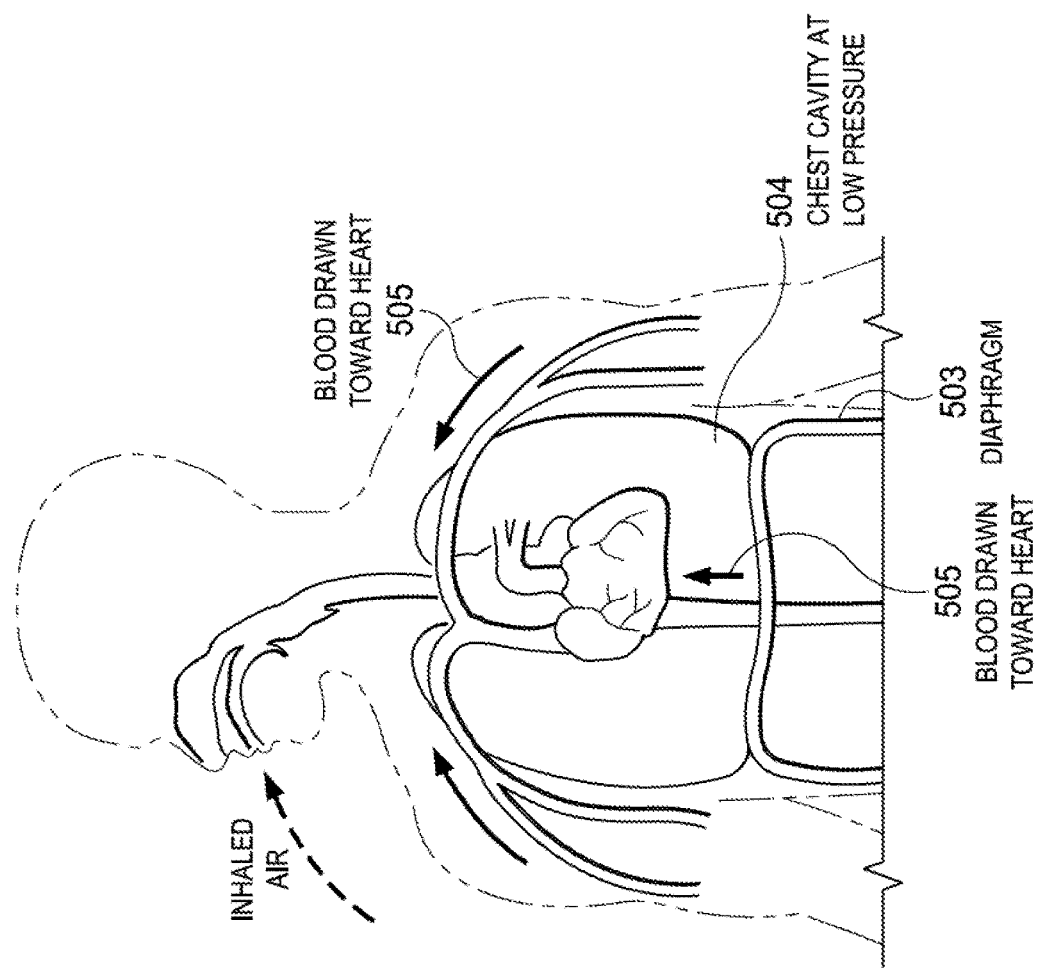
FIG. 5A is a diagram of a venous return during a respiratory pump.

Referring to FIGS. 5A and 5B, the venous return/signal (e.g., back flow of blood to the heart) is mainly due to skeletal muscle pump and respiratory pump. When muscles contract, one way valves open and when muscles relax valves close to prevent back flow of blood. Open valve 501 during muscle contraction 502 is shown in FIG. 5b. Another main contributing factor in pulsating venous return is the respiratory pump which causes compression and decompression of veins. During inhalation, diaphragm 503 moves downward which causes a low pressure state in thoracic cavity 504 and high pressure abdominal cavity. Hence, the abdominal veins are compressed and blood moves to decompressed thoracic and to the right atrium of the heart at 505. Pressure reverses during exhalation and valves prevent back flow of the blood. Therefore, blood flow in veins is affected by respiration and one of the applications of the separation of arterial and venous signals is extraction of respiratory related information.

Figure 6:
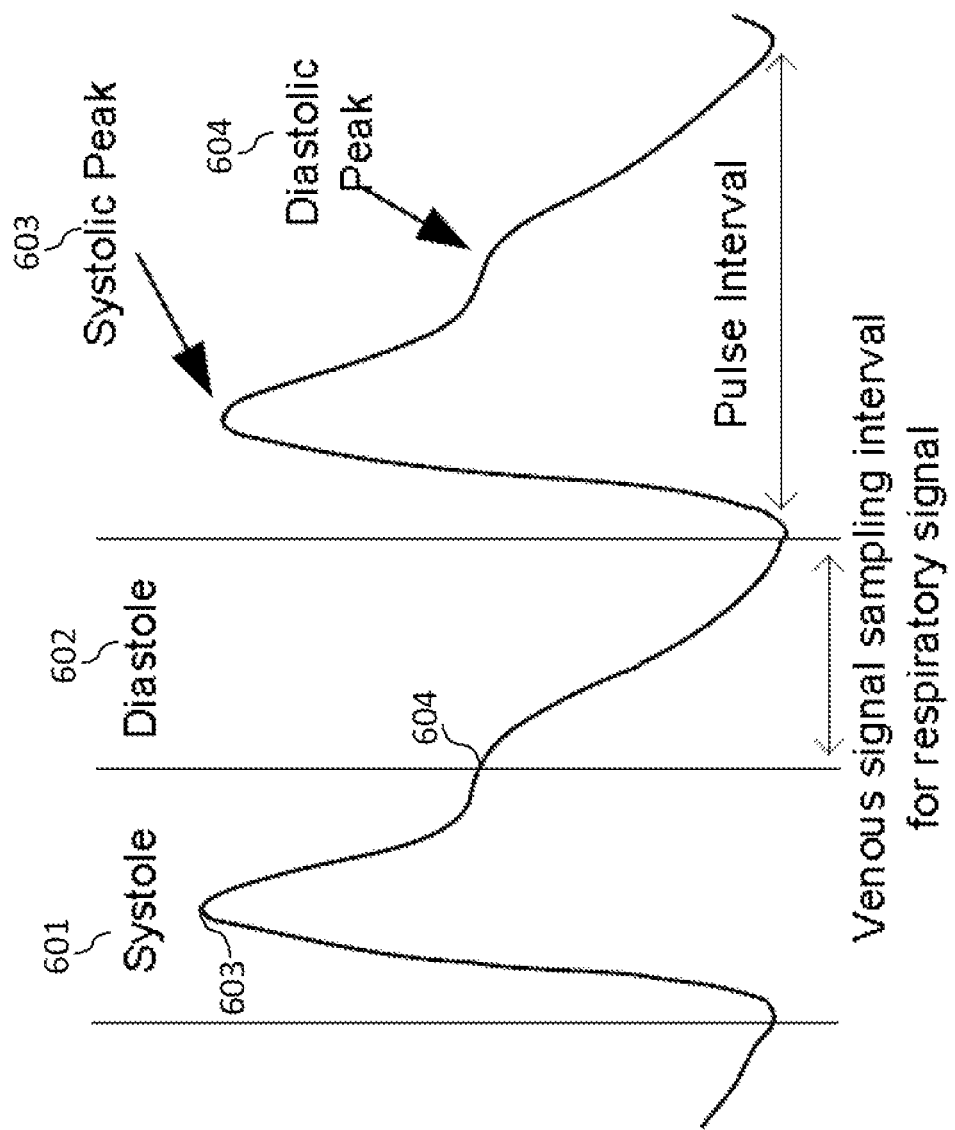
FIG. 6 is a graph of a venous signal sampling for respiratory signal extraction.

In order to extract the respiratory signal, beat-to-beat variation of the venous return signal using a cardiac gating approach is employed. Referring to FIG. 6, the biphasic activity of cardiac cycle includes systole portion 601 and diastole portion 602. Systole portion 601 has systolic peaks 603. Diastole portion 602 has diastolic peaks 604. The venous signal is sampled during diastole portion 602 for extracting the respiratory signal.

Figure 7A:
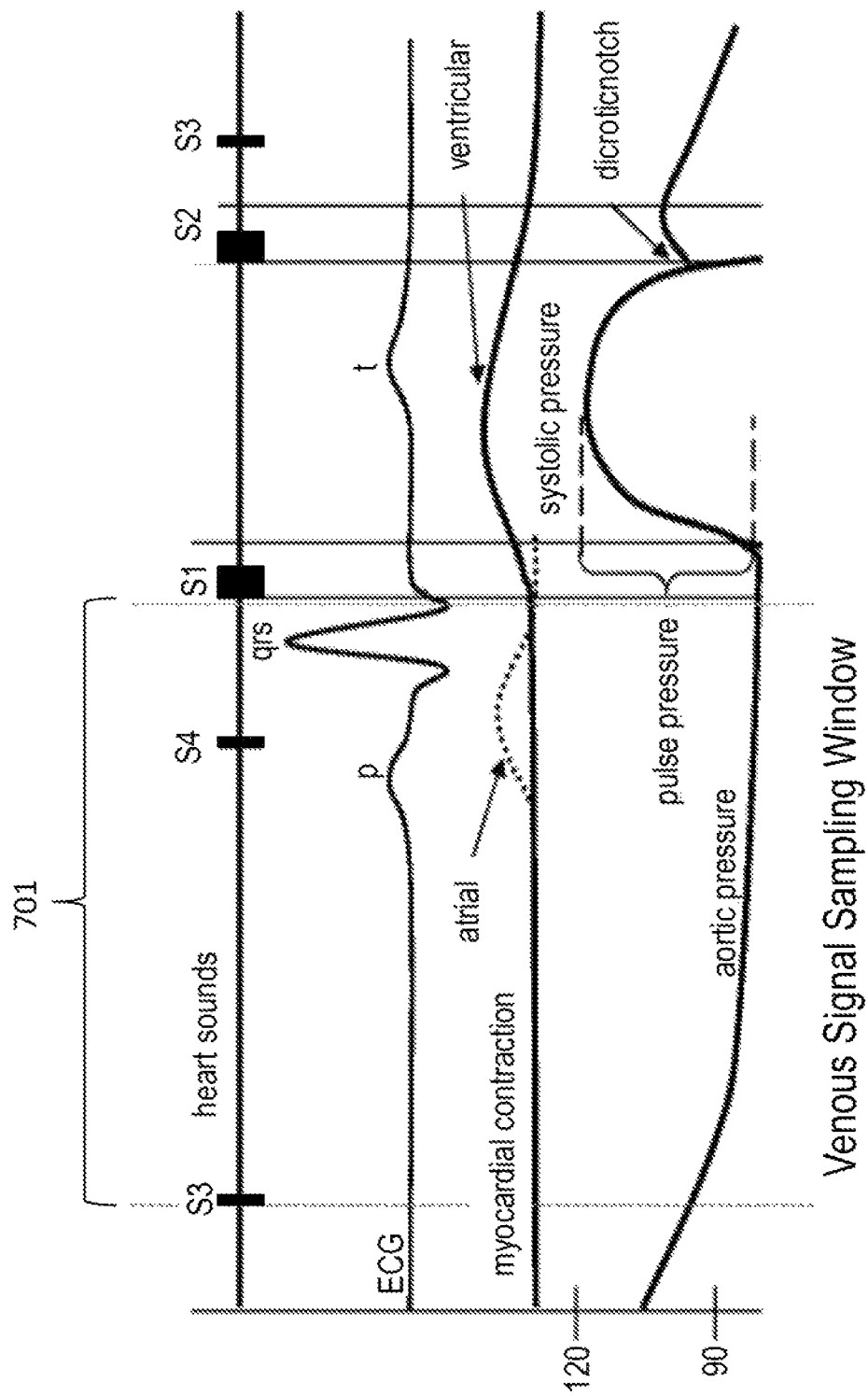
FIG. 7A is a graph of a venous signal sampling window.

Referring to FIGS. 7a, 7b, and 7c, different activities during a cardiac cycle are shown. When the ventricular is not contracted during diastole 701, the arterial blood flow and hydrodynamic pressures are minimum. Decreased blood pressure during diastole 701 results in a weak and low amplitude arterial signal. During this time duration, the venous return is still in progress by both respiratory and skeletal muscle pumps. The arterial signal may be considered as an interference added to the venous signal, and the diastole time duration is the interference or noise-free portions 702, 703, and 704 of the biphasic cardiac cycle. Therefore, the noise-free portions 702, 703, and 704 of the extracted venous signal in each cardiac cycle may be sampled to extract the respiratory signal.

FIG. 7b shows sampling windows 702 and 703 of interest during consecutive cardiac cycles. An algorithm is used to determine the active sampling window in each cardiac cycle, which will be further described.

FIG. 7c shows active time duration of sampling during a signal cardiac cycle. During sampling window 704 venous pressure 705 changes rapidly to its maximum value at point 706 while arterial signal 707 has a low amplitude at point 708. Respiration changes the morphological features of this upward back flow of the blood return including maximum signal value at point 706.

Figure 8:
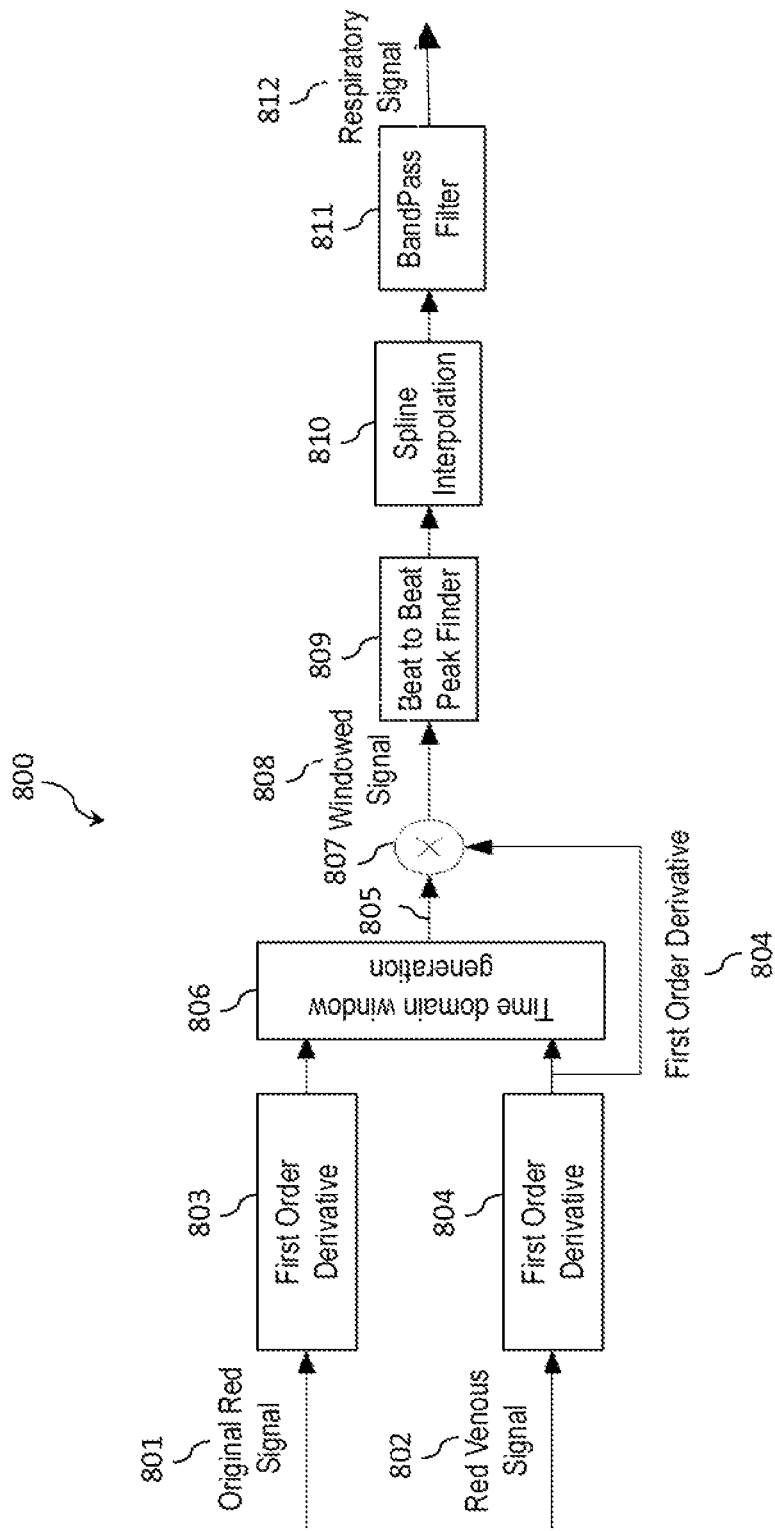
FIG. 8 is a schematic of respiratory signal extraction using a cardiac gated venous return signal.

Referring to FIG. 8, step 210 (of FIG. 2B) is further described as method 800 for cardiac gating of extracted venous signal and extracting respiratory signal. In method 800, first derivatives 803 and 804 of original red signal 801 and extracted red venous signal 802, respectively, are taken. Time domain window signal 805 whose value is 1 during diastole and zero elsewhere is created. Time domain window signal 805 is created using time domain window generation 806 as follows: If first order derivative 803 of original red signal 801 is greater than zero, then time domain window signal 805 takes zero value. Otherwise, time domain window signal 805 remains one. This operation makes the starting point of the PPG signal up to peak systolic points of the window zero in each cardiac cycle. Next, if first order derivative 804 of extracted red venous signal 802 is less than zero, the corresponding time domain window signal 805 becomes zero. This operation will remove the time duration between systolic peak and diastolic peak pressures. After creating time domain window signal 805, which implements the cardiac gating approach, time domain window signal 805 is multiplied with first order derivative 804 of extracted red venous signal 802 with multiplier 807 into windowed first order derivative venous signal 808. Then, in each beat cycle and during diastole, peak finder 809 finds the maximum amplitude of windowed first order derivative venous signal 808. The peak value of windowed first order derivative venous signal 808 will change as the respiratory pump changes the venous return in every beat cycle. Sampling rate of the extracted respiratory induced venous return variations is lower compared to original signal. In fact, there is one sample per cardiac cycle, hence spline interpolator 810 is used to interpolate the extracted variation by implementing a polynomial interpolation, preferably a spline interpolation, and filtered with band pass filter 811 to limit the frequency content of the output signal to preferably the typical frequency of human respiration rate (e.g. 4 breaths per minute to 40 breaths per minute for adults), to build respiratory signal 812.

Test 1

An experimental platform is developed using finger and forehead probes with red and infrared LEDs. Analog conditioning circuit limits the bandwidth of the signal to 70 Hz and data is acquired with sampling rate of 150 Hz using a TMS320C5515 processor by Texas Instruments. Method 200 removes the venous component from red and infrared signals and provides arterial red and arterial infrared signals. So, the ratio of red to infrared signal is computed using arterial signals by Eq. 1. After extraction of ratio R an empirical calibration curve is used to compute the arterial oxygen saturation level $SpO_2$.

A prominent venous component can cause inaccurate $SpO_2$ readings and the power of the venous component varies in different locations of the body. So, venous effect is location sensitive. For example, forehead sensors are shown to be more sensitive to venous return signal. Further, for the same measurement site, the power of the venous component may change over time depending on volume of blood return due to motion, respiration, etc. The proven causes of venous return change are skeletal muscle pumping and respiratory pumping as previously discussed. Therefore, in order to change venous return and see the effect of venous return signal changes on the "ratio of ratios" (i.e. $SpO_2$), we can either change the respiratory pump component or skeletal muscle pump. Skeletal muscle pumping can be changed by motion or exercise. Rate of flow through exercising skeletal muscles can be 15 to 20 times greater than resting muscles. Despite the dramatic change of venous return signal during exercise, the motion artifact significantly reduces the signal quality and changes will be buried in noise. Therefore, the effect of such changes on "ratio of ratios" or related $SpO_2$ cannot be easily studied. Hence, an experiment was designed to validate method 200 in terms of removal of venous related inaccuracies in "ratio of ratios" measurement. In this experiment, data was collected from twelve subjects from both a finger sensor and a forehead sensor, simultaneously. Twenty minutes of data was collected from each subject. In order to change venous return, subjects were required to change respiration rate over time in a wide range.

Figure 9:
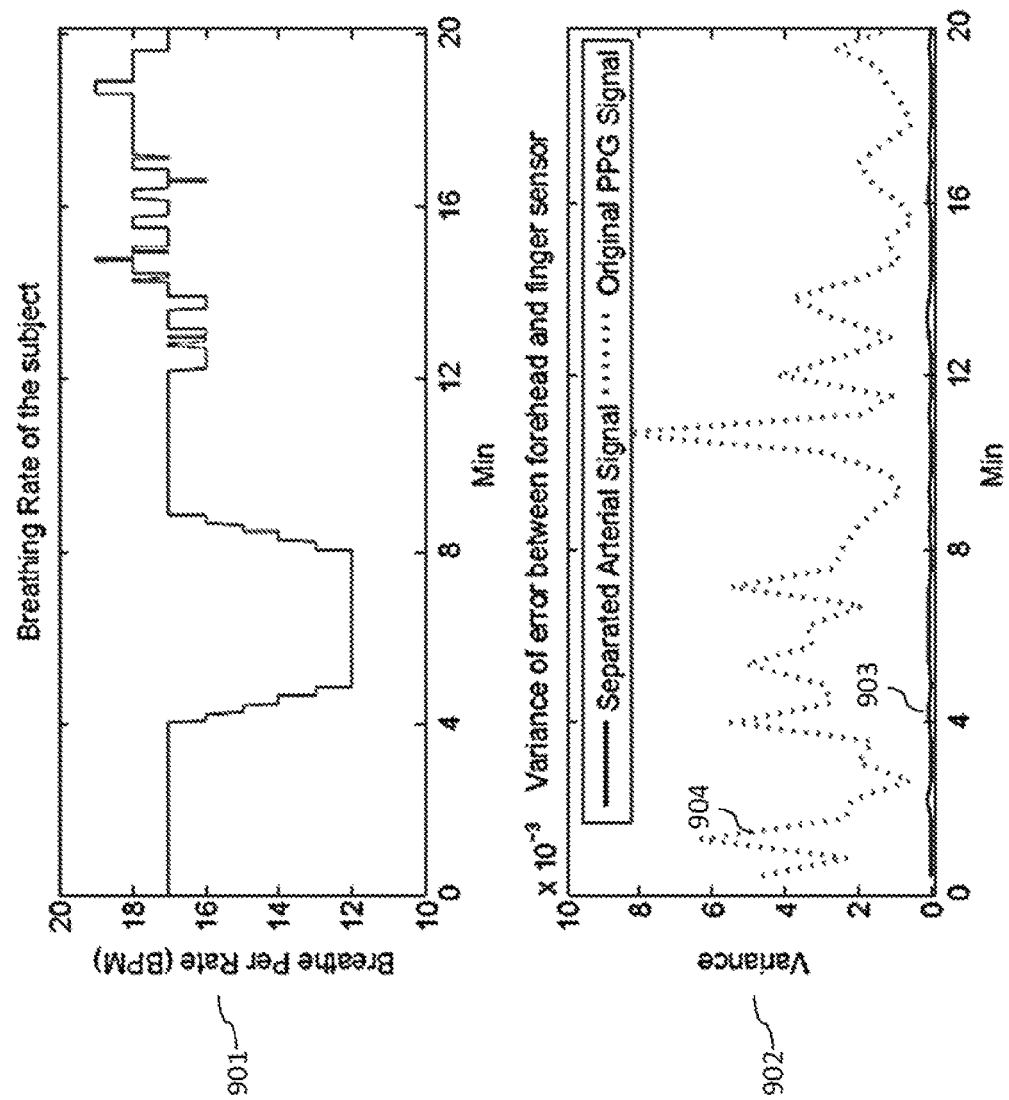
FIG. 9 is a set of graphs for a breathing rate and a variance of error due to respiratory induced venous return changes.

Referring to FIG. 9, the pattern of respiratory rate changes over the course of the experiment for one of the subjects is shown in graph 901 and the corresponding variance of difference between readings from forehead and finger sensors is shown in graph 902. In graph 902 variance of error between forehead and finger "ratio of ratios" is computed every 26 seconds. The variance of the error is much less for method 200 plotted as curve 903 than for original PPG signal curve 904, which means that despite changes in venous signal due to respiration, method 200 gives similar readings at the output.

Table 1 below summarizes the variance of difference between readings using method 200 and standard "ratio of ratios" on original PPG signal for all subjects. Since method 200 separates the arterial component and the ratio is computed based on arterial component, method 200 significantly reduces the error between forehead and finger sensors.

TABLE 1

VARIANCE OF RATIO DIFFERENCE BETWEEN FOREHEAD AND FINGER SENSOR

| Methods | \multicolumn{12}{c}{Subjects} | |
|---|---|---|---|---|---|---|---|---|---|---|---|---|
| | M-32 | M-44 | M-50 | F-29 | M-29 | M-21 | M-31 | F-50 | M-59 | F-41 | F-29 | M-25 | Average |
| Prior Art Method | 0.003 | 0.020 | 0.040 | 0.017 | 0.032 | 0.086 | 0.008 | 0.019 | 0.0235 | 0.035 | 0.078 | 0.053 | 0.04 |
| Method 200 | 2.0e−5 | 1.07e−4 | 1.3e−4 | 7.23e−5 | 4.5e−4 | 3.53e−4 | 7.12e−5 | 5.4e−5 | 4.34e−5 | 1.81e−5 | 3.42e−5 | 0.51e−4 | 1.3e−4 |

Method 200 extracts the venous signal and is employed to provide other features related to venous signal, including the extraction of a respiratory signal in step 210. In step 211, the respiration rate (number of breaths per minute) is extracted from the respiratory signal.

Figure 10:
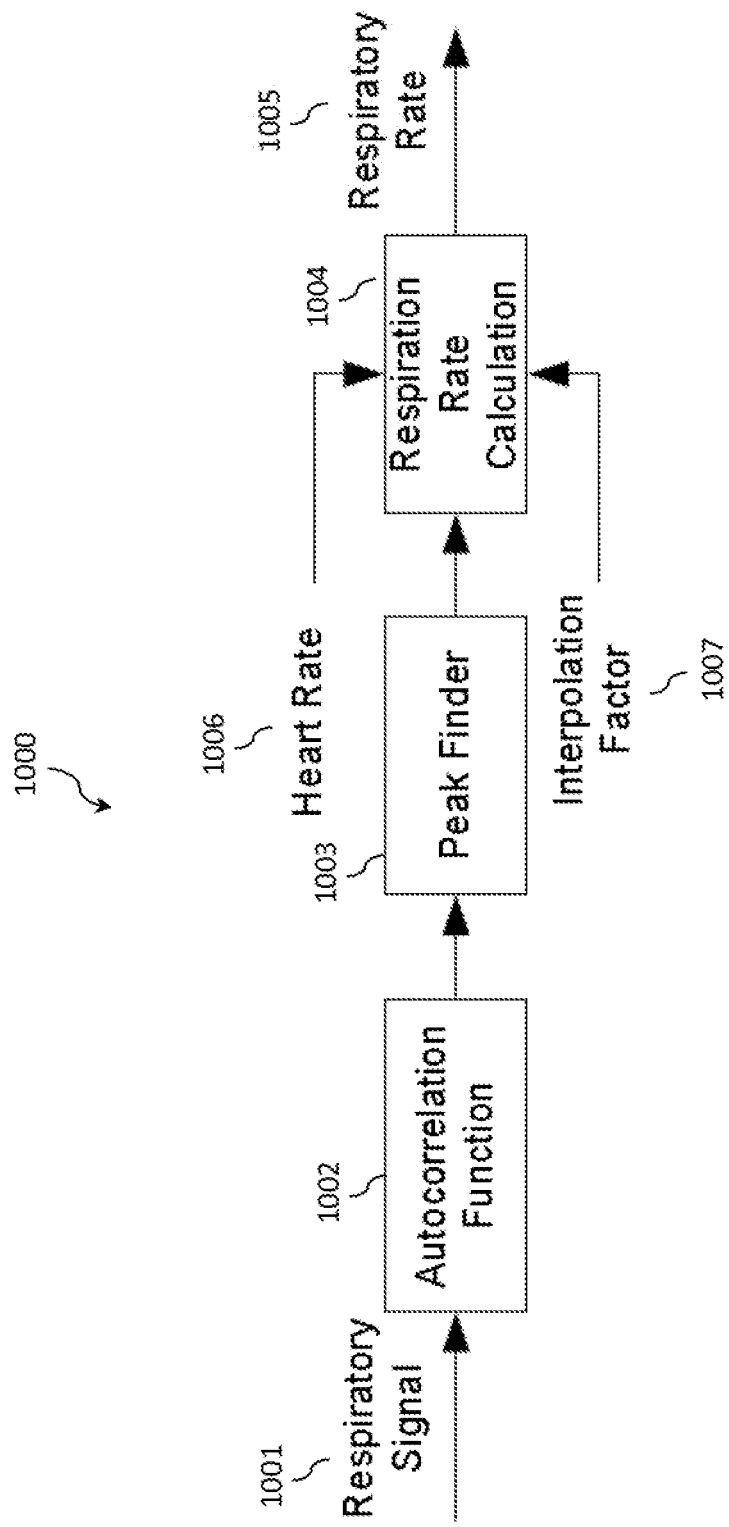
FIG. 10 is a flow chart of a method for correlation-based respiration rate extra oil.

Referring to FIG. 10, step 211 (of FIG. 2B) is further described as method 1000 for respiration rate extraction. At step 1002, an autocorrelation function is computed using respiratory signal 1001 in the lag range corresponding to a human respiration rate range, e.g., 4 breaths per minute to 40 breaths per minute for adults. At step 1003, the first dominant peak of the autocorrelation function is found by detection of all local peaks and selecting the peak with highest amplitude. At step 1004, the fundamental period corresponding to the first peak is divided by interpolation factor 1007 and provides the number of heart beats (cardiac cycles) in a single respiratory cycle (inspiration and expiration). In this step, heart rate per minute 1006 is divided by the number of beats per respiratory cycle provides respiratory rate per minute 1005.

Test 2

In this experiment, data is collected from 12 subjects. Each subject wore a finger sensor and the PPG signals from each sensor are captured for twenty minutes. Simultaneously, the respiration rate of each subject is monitored and recorded using a commercial reference sensor.

Accuracy of method 1000 is summarized in Table 2 below. The average Root Mean Square Deviation (RMSD), i.e., the measure of difference between calculated and reference respiration rates, is 1.89 breaths per minute and average standard deviation is 1.54. Average Mean of Difference (Diff. Mean) and Mean of Absolute Value of Difference (Abs. Diff. Mean) for 12 subjects are −0.69 and 1.26 breaths per minutes, respectively. The experimental results show that the separated venous component has the respiratory pump and respiratory induced venous return variation. Further, the respiratory signal was extracted from the separated venous signal and finally, the respiration rate was computed from the respiratory waveform.

TABLE 2

BREATHING RATE ACCURACY

| Parameter | M-32 | M-44 | M-50 | F-29 | M-29 | M-21 | M-31 | F-50 | M-59 | F-41 | F-29 | M-25 | Average |
|---|---|---|---|---|---|---|---|---|---|---|---|---|---|
| RMSD | 0.87 | 2.03 | 1.87 | 2.05 | 1.54 | 2.06 | 2.45 | 1.17 | 2.66 | 2.17 | 2.35 | 1.56 | 1.89 |
| Diff. Mean | −0.28 | −0.56 | −0.35 | −1.27 | −0.83 | 0.12 | −1.26 | 0.61 | −1.89 | −1.27 | −0.97 | −0.30 | −.69 |
| Abs. Diff. Mean | 0.65 | 1.32 | 0.79 | 1.65 | 1.08 | 1.43 | 1.57 | 0.92 | 1.95 | 1.38 | 1.24 | 1.23 | 1.26 |
| St. Dev | 0.82 | 1.95 | 1.12 | 1.6 | 1.29 | 2.05 | 2.10 | 1.00 | 1.87 | 1.76 | 1.36 | 1.53 | 1.54 |

The experimental results show that compared to standard techniques, the variance of difference between forehead and finger sensor is negligible. This enables a measurement site with independent and accurate arterial oxygen saturation monitoring. The experimental results shows that on average the respiration rate can be computed with 1.89 RMSD compared to commercially available technologies.

It will be appreciated by those skilled in the art that the described embodiments disclose significantly more than an abstract idea including technical advancements in the fields of healthcare, human health monitoring, and human circulation system monitoring, and a transformation of data which is directly related to real world objects and situations. Specifically, the disclosed embodiments generate respiratory, blood oxygen, and respiratory signals by detecting artery, vein, and tissue movements and transforming such movements into a set of photoplethysmographic signals. The set of photoplethysmographic signals are then transformed into identifiable and usable arterial and venous signal. The arterial and venous signal are then transformed into a blood oxygen level and a respiratory rate to determine the health of a human patient.

It will be appreciated by those skilled in the art that modifications can be tirade to the embodiments disclosed and remain within the inventive concept. Therefore, this invention is not limited to the specific embodiments disclosed, but is intended to cover changes within the scope and spirit of the claims.

The invention claimed is:

1. A method for extracting arterial, venous, blood oxygen, and respiratory information from a set of photoplethysmographic signals comprising the steps of:
   preprocessing the set of photoplethysmographic signals;
   locating a venous signal and an arterial signal in each photoplethysmographic signal of the set of photoplethysmographic signals, using second order blind identification;
   extracting the arterial signal and the venous signal from each photoplethysmographic signal of the set of photoplethysmographic signals;
   extracting a respiratory signal using the venous signal and the arterial signal; and,
   extracting a blood oxygen saturation from the arterial signal;
   wherein the set of photoplethysmographic signals comprises a red signal and an infrared signal;

wherein the red signal comprises a red venous signal and a red arterial signal; and, wherein the step of extracting a respiratory signal further comprises the steps of:

determining a red signal derivative of the red signal;

determining a red venous signal derivative for the red venous signal;

generating a time domain window signal from the red signal derivative and the red venous signal derivative;

generating a windowed signal from the time domain window signal and the red venous signal derivative;

determining a maximum amplitude from the windowed signal;

determining a venous return variation from the maximum amplitude;

interpolating the venous return variation; and, filtering the venous return variation to generate the respiratory signal.

2. The method of claim 1, further comprising the steps of:

computing an autocorrelation function of the respiratory signal;

determining a peak of the autocorrelation function; and, calculating a respiratory rate using the peak.

3. The method of claim 1, wherein the step of extracting the arterial signal further comprises the steps of:

determining a venous reference signal from the set of photoplethysmographic signals;

filtering the arterial signal from each photoplethysmographic signal of the set of photoplethysmographic signals, using the venous reference signal; and, filtering the venous signal from each photoplethysmographic signal of the set of photoplethysmographic signals, using the venous reference signal.

4. The method of claim 3, further comprising the steps of:

extracting a fundamental frequency from the arterial signal; and, filtering the venous signal using the fundamental frequency.

5. The method of claim 1, wherein the step of preprocessing further comprises the step of filtering the set of photoplethysmographic signals with a low pass filter.

6. The method of claim 1, wherein the step of locating further comprises the steps of:

whitening the set of photoplethysmographic signals; and, computing an approximate joint diagonalization of the set of photoplethysmographic signals.

7. A method for extracting a respiratory signal and a blood oxygen level from a red photoplethysmographic signal and an infrared photoplethysmographic signal comprising the steps of:

receiving the red photoplethysmographic signal and the infrared photoplethysmographic signal;

filtering the red photoplethysmographic signal and the infrared photoplethysmographic signal;

separating the red photoplethysmographic signal into a first signal component and a second signal component;

separating the infrared photoplethysmographic signal into a third signal component and a fourth signal component;

determining a red venous signal from the first signal component and a red arterial signal from the second signal component;

determining an infrared venous signal from the third signal component and an infrared arterial signal component from the fourth signal component;

extracting the red arterial signal and the red venous signal from the red photoplethysmographic signal;

extracting the infrared arterial signal and the infrared venous signal from the infrared photoplethysmographic signal;

extracting the respiratory signal using the red photoplethysmographic signal and the red venous signal; and, extracting the blood oxygen signal using the red arterial signal and the infrared arterial signal;

wherein the step of extracting the respiratory signal further comprises the steps of:

determining a red signal derivative of the red photoplethysmographic signal;

determining a red venous signal derivative of the red venous signal;

generating a time domain window signal from the red signal derivative and the red venous signal derivative;

generating a windowed signal from the time domain signal and the red venous signal derivative;

determining a maximum amplitude from the windowed signal;

determining a venous return variation from the maximum amplitude;

interpolating the venous return variation; and, filtering the venous return variation to generate the respiratory signal.

8. The method of claim 7, further comprising the steps of:

computing an autocorrelation function of the respiratory signal;

determining a peak of the autocorrelation function; and, calculating a respiratory rate using the peak.

9. The method of claim 7, wherein the step of extracting the red arterial signal and the red venous signal further comprises the steps of:

determining a venous reference signal from the red photoplethysmographic signal and the infrared photoplethysmographic signal;

filtering the red arterial signal from the red photoplethysmographic signal using the venous reference signal; and, filtering the red venous signal from the red photoplethysmographic signal using the venous reference signal.

10. The method of claim 9, wherein the step of extracting the infrared arterial signal and the infrared venous signal further comprises the steps of:

determining the venous reference signal from the red photoplethysmographic signal and the infrared photoplethysmographic signal;

filtering the infrared arterial signal from the infrared photoplethysmographic signal using the venous reference signal; and, filtering the infrared venous signal from the infrared photoplethysmographic signal using the venous reference signal.

11. The method of claim 10, further comprising the steps of:

extracting a fundamental frequency from the infrared arterial signal;

filtering the red venous signal using the fundamental frequency; and filtering the infrared venous signal using the fundamental frequency.

12. A system for extracting arterial, venous, blood oxygen, and respiratory information from a set of photoplethysmographic signals comprising:

an extractor;
a set of photoplethysmographic sensors outputting a set of photoplethysmographic signals, each photoplethysmographic sensor connected to the extractor;
a computing device connected to the extractor and programmed to:
preprocess the set of photoplethysmographic signals;
locate a venous signal and an arterial signal in each photoplethysmographic signal of the set of photoplethysmographic signals using second order blind identification;
extract the arterial signal and the venous signal from each photoplethysmographic signal of the set of photoplethysmographic signals;
extract a respiratory signal using the venous signal and the arterial signal; and,
extract a blood oxygen saturation from the arterial signal;
wherein each photoplethysmographic sensor comprises a red LED and an infrared LED;
wherein the set of photoplethysmographic signals comprises a red signal and an infrared signal;
wherein the red signal further comprises a red venous signal and a red arterial signal; and,
wherein the computing device is further programmed to:
receive the red signal from the red LED;
receive the infrared signal from the infrared LED;
determine a red signal derivative of the red signal;
determine a red venous signal derivative for the red venous signal;
generate a time domain window signal from the red signal derivative and the red venous signal derivative;
generate a windowed signal from the time domain signal and the red venous signal derivative;
determine a maximum amplitude from the windowed signal;
determine a venous return variation from the maximum amplitude;
interpolate the venous return variation; and,
filter the venous return variation to generate the respiratory signal.

13. The system of claim 12, wherein the computing device is further programmed to:
compute an autocorrelation function of the respiratory signal;
determine a peak of the autocorrelation function; and,
calculate a respiratory rate using the peak.

14. The system of claim 12, wherein the computing device is further programmed to:
determine a venous reference signal from the set of photoplethysmographic signals;
filter the arterial signal from each photoplethysmographic signal of the set of photoplethysmographic signals using the venous reference signal; and,
filter the venous signal from each photoplethysmographic signal of the set of photoplethysmographic signals using the venous reference signal.

15. The system of claim 14, wherein the computing device is further programmed to:
extract a fundamental frequency from the arterial signal; and,
filter the venous signal using the fundamental frequency.

16. The system of claim 12, wherein the extractor further comprises a set of filters, and wherein the computing device is further programmed to filter the set of photoplethysmographic signals with the set of filters.

17. The system of claim 12, wherein the computing device is further programmed to:
whiten the set of photoplethysmographic signals; and,
compute an approximate joint diagonalization of the set of photoplethysmographic signals.

* * * * *